(12) United States Patent
Muraskin et al.

(10) Patent No.: US 10,299,695 B2
(45) Date of Patent: May 28, 2019

(54) SYSTEMS AND METHODS FOR IDENTIFYING AND TRACKING NEURAL CORRELATES OF BASEBALL PITCH TRAJECTORIES

(71) Applicant: The Trustees of Columbia University in the City of New York, New York, NY (US)

(72) Inventors: Jordan Muraskin, New York, NY (US); Jason Sherwin, New York, NY (US); Paul Sajda, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 989 days.

(21) Appl. No.: 14/612,233

(22) Filed: Feb. 2, 2015

(65) Prior Publication Data
US 2016/0242669 A1 Aug. 25, 2016

Related U.S. Application Data

(63) Continuation-in-part of application No. 14/598,905, filed on Jan. 16, 2015, now abandoned, which is a
(Continued)

(51) Int. Cl.
| | |
|---|---|
| A61B 5/00 | (2006.01) |
| A61B 5/0484 | (2006.01) |
| A61B 5/04 | (2006.01) |
| A61B 5/0478 | (2006.01) |
| A61B 5/0482 | (2006.01) |

(Continued)

(52) U.S. Cl.
CPC ........ *A61B 5/04842* (2013.01); *A61B 5/0075* (2013.01); *A61B 5/04012* (2013.01); *A61B 5/0478* (2013.01); *A61B 5/0059* (2013.01); *A61B 5/0482* (2013.01); *A61B 5/055* (2013.01); *A61B 5/742* (2013.01); *A61B 2503/10* (2013.01);
(Continued)

(58) Field of Classification Search
CPC .................................................. A61B 5/0476
See application file for complete search history.

(56) References Cited

U.S. PATENT DOCUMENTS

| | | | |
|---|---|---|---|
| 6,032,108 A | 2/2000 | Seiple et al. | |
| 7,771,320 B2 | 8/2010 | Riley et al. | |

(Continued)

OTHER PUBLICATIONS

U.S. Appl. No. 14/598,905, dated Dec. 15, 2017 Non-Final Office Action.
(Continued)

*Primary Examiner* — Christian Jang
(74) *Attorney, Agent, or Firm* — Baker Botts L.L.P.

(57) ABSTRACT

Methods and systems for evaluating a subject's response to a task related to a stimulus include a brain activity sensor, such as an EEG sensor, for measuring neural data generated by the subject in response to the visual stimulus. One or more neural discriminators can be calculated based on the neural data. In order to generate one or more neural discriminators, two or more task conditions can be selected for discrimination. The subject's performance can be evaluated based on the one or more neural discriminators. Feedback can be provided to the subject to assist in achieving better performance.

10 Claims, 20 Drawing Sheets

Related U.S. Application Data continuation of application No. PCT/US2013/053505, filed on Aug. 2, 2013.

(60) Provisional application No. 61/729,819, filed on Nov. 26, 2012, provisional application No. 61/678,904, filed on Aug. 2, 2012.

(51) Int. Cl.
  *G01R 33/48* (2006.01)
  *A61B 5/055* (2006.01)

(52) U.S. Cl.
  CPC .... *A61B 2576/026* (2013.01); *G01R 33/4806* (2013.01)

(56) References Cited

U.S. PATENT DOCUMENTS

| | | | |
|---|---|---|---|
| 8,152,693 B2 | 4/2012 | Nurmela et al. | |
| 8,152,695 B2 | 4/2012 | Riley et al. | |
| 2007/0106170 A1* | 5/2007 | Dunseath, Jr. | A61B 5/0478 600/544 |
| 2008/0004544 A1* | 1/2008 | Caplygin | A61B 5/168 600/558 |
| 2008/0243005 A1* | 10/2008 | Jung | A61B 5/16 600/481 |
| 2009/0210078 A1 | 8/2009 | Crowley | |
| 2009/0270693 A1* | 10/2009 | Hyde | A61B 5/024 600/301 |
| 2009/0326404 A1 | 12/2009 | Sajda et al. | |
| 2011/0218950 A1 | 9/2011 | Mirowski et al. | |
| 2011/0245708 A1 | 10/2011 | Finkel et al. | |

OTHER PUBLICATIONS

U.S. Appl. No. 14/598,905, dated Oct. 5, 2017 Response to restriction Requirement.

U.S. Appl. No. 14/598,905, dated Jun. 26, 2017 Restriction Requirement.

U.S. Appl. No. 14/598,905 (Now U.S. Pat. No. 2015/0216439), filed Jan. 16, 2015 (dated Aug. 6, 2015).

International Search Report dated Nov. 8, 2013 in PCT/US2013/053505.

* cited by examiner

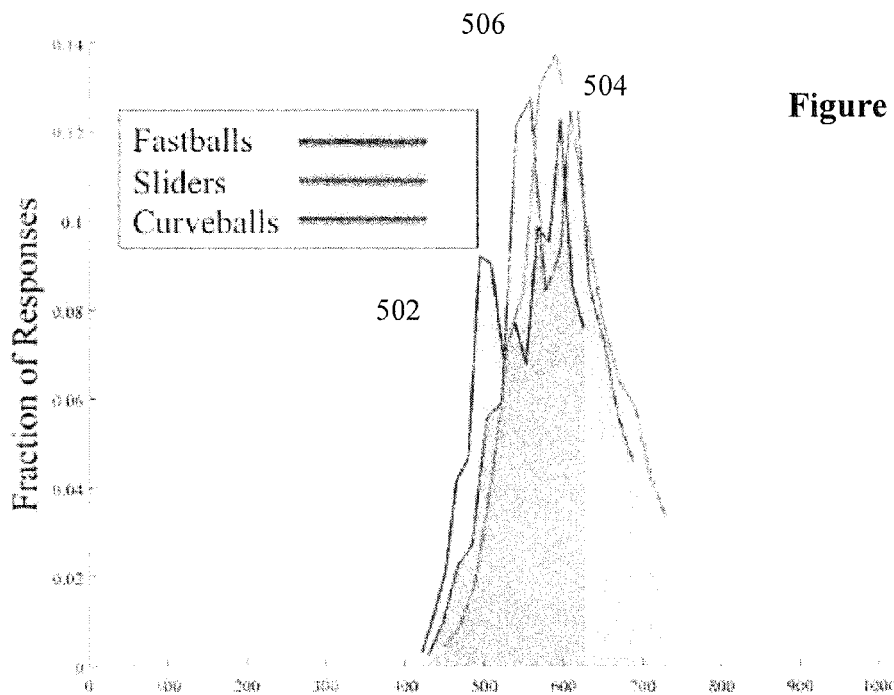
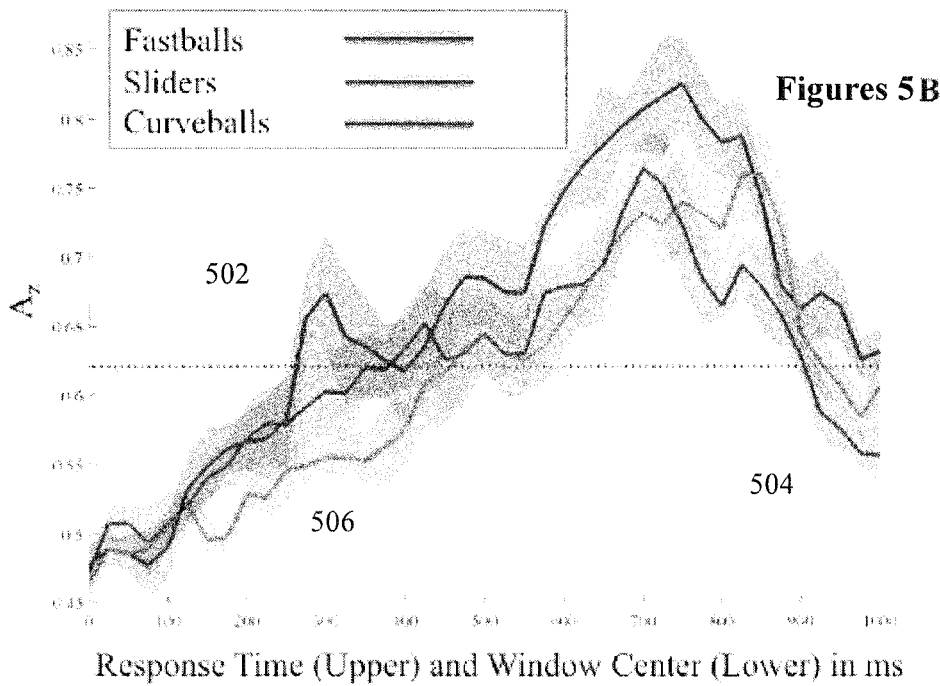
Response Time (Upper) and Window Center (Lower) in ms

Note: Baseball Diamond Objects Not to Scale

SYSTEMS AND METHODS FOR IDENTIFYING AND TRACKING NEURAL CORRELATES OF BASEBALL PITCH TRAJECTORIES

CROSS-REFERENCE TO RELATED APPLICATIONS

This application is a continuation-in-part of U.S. patent application Ser. No. 14/598,905 filed Jan. 16, 2015, which is a continuation of International Patent No. PCT/US13/053505, filed Aug. 2, 2013, which claims priority to Provisional Application Ser. No. 61/678,904 filed on Aug. 2, 2012, and U.S. Provisional Application Ser. No. 61/729,819 filed on Nov. 26, 2012, each of which are incorporated herein by reference for all purposes.

STATEMENT REGARDING FEDERALLY SPONSORED RESEARCH

This invention was made with government support under grant MH085092 awarded by the National Institutes of Health, and grant W911NF-11-1-0219 awarded by the Army Research Laboratory—Army Research Office. The Government has certain rights in this invention.

BACKGROUND

In baseball, a hitter has a fraction of a second to decide whether the pitch will be a ball or a strike and to decide whether to swing at the pitch. Thus, hitters rely on rapid decision-making processes that track the trajectory and speed of the ball with sufficient accuracy to predict its location when it crosses the plate and decide on an appropriate motor response. Due to the different speeds and trajectories that pitches can follow, it can be difficult for batters to guess a pitch and maintain accuracy. One element of the rapid decision making process is determining what type of pitch is thrown, e.g., a fastball, curveball, or a slider, because the type of pitch constrains the potential trajectories of the ball.

There have been certain attempts to examine the pitch classification process using behavioral/psychological markers. For instance, eye movements before and after pitches have been used to identify visual search strategies employed by expert vs. novice players. Certain findings show that experts focused their visual (spatial) attention closer to the estimated release point of the pitch, when compared to novices, suggesting that earlier trajectory tracking can be crucial for batting performance. Furthermore, the middle third of a pitch's trajectory can be the most predictive of whether subjects made contact with a pitched softball.

In "Perceptual Decision Making for Baseball Pitch Recognition: Using P300 Latency and Amplitude to Index Attentional Processing," Radlo et al. used EEG data to examine the perceptual and attentional processes associated with the effects of administering a cost-benefit precuing paradigm to intermediate and advance-level baseball batters. However, that study used a single raw data item—P300—to investigate perceptual decision making.

SUMMARY

In one aspect, the disclosed subject matter provides a method for evaluating a subject's response when presented with a task related to a stimulus having a trajectory. The method can include measuring, using an electronic brain activity sensor, neural response data generated by the subject when presented with a task related to a stimulus having a trajectory, identifying one or more neural discriminators associated with the task based on the neural response data, and evaluating the subject's response based at least in part on the one or more neural discriminators.

In accordance with one embodiment of the disclosed subject matter, the stimulus can be a baseball pitch. The baseball pitch can be a live baseball pitch, a recorded baseball pitch, or a simulated baseball pitch. The task can be choosing a type of pitch or hitting the pitch.

Identifying the one or more neural discriminators can include calculating a neural discriminator that discriminates between a first task condition and a second task condition. In an exemplary embodiment of the disclosed subject mater, the first task condition can be a correct decision and the second task condition can be an incorrect decision. In another embodiment of the disclosed subject matter, the first task condition can be a first correct decision and the second task condition can be a second correct decision. The method can further include calculating a vector. The vector can be calculated using logistic regression.

In accordance with an exemplary embodiment of the disclosed subject matter, evaluating the subject's performance can include determining when during the trajectory the subject makes a decision related to the task. The decision can be, for example, an identification of a pitch type. The method can further include providing feedback to the subject or identifying an active neural source associated with the neural discriminator.

In a second aspect, the disclosed subject matter provides a system for evaluating a subject's response when presented with a task related to a stimulus having a trajectory. The system can include a brain activity sensor configured to measure neural response data generated by a subject when presented with a task related to a stimulus having a trajectory, a signal processing system comprising at least one processor configured to identify one or more neural discriminators associated with the task based on the neural response data, and an output device for providing information based on the neural discriminators for purposes of evaluation.

In accordance with an exemplary embodiment of the disclosed subject matter, the brain activity sensor can be an array of brain activity sensors. The brain activity sensor can include an electroencephalography sensor. The brain activity sensor can also include a near infrared sensor or a functional magnetic resonance imaging sensor. The output device can be, for example, a printer or a monitor.

In another aspect, the disclosed subject matter can provide a system for evaluating a subject's response when presented with a task related to a stimulus having a trajectory including a brain activity sensor, at least one processor, a non-transitory computer-readable medium, and an output device. The brain activity sensor can be configured to measure neural response data generated by the subject when presented with a task related to a stimulus having a trajectory. The non-transitory computer-readable medium can store instructions that, when implemented, cause the at least one processor to identify one or more neural discriminators associated with the task based on the neural response data. The output device can provide information based on the neural discriminators for purposes of evaluation.

The accompanying drawings, which are incorporated and constitute part of this disclosure, illustrate the various exemplary embodiments of the present disclosed subject matter and serve to explain its principles.

BRIEF DESCRIPTION OF THE DRAWINGS

FIG. 4A illustrates mean behavioral responses for accuracy and positive predictive value, and FIG. 4B illustrates mean response times for correctly and incorrectly identified pitches.

FIG. 5A-5B illustrates results for each pitch averaged across subjects in accordance with an exemplary embodiment of the disclosed subject matter. FIG. 5A illustrates behavioral results, and FIG. 5B illustrates stimulus-locked EEG discrimination results. Fastballs are plotted at 502, sliders are plotted at 504, and curveballs are plotted at 506.

FIG. 9A illustrates a dugout view, and FIG. 9B illustrates a catcher's view.

FIG. 17A-17E illustrates t-distribution based on a paired t-test illustrates the time series of experts versus novices for Go trials in accordance with an exemplary embodiment of the disclosed subject matter. FIG. 17A shows the results for Correct Go versus Correct No-Go across both experts and novices. FIG. 17B shows the results between experts and novices between Correct Go versus Correct No-Go trials. FIG. 17C shows the results between experts and novices for Correct Go trials. FIG. 17D shows the results between experts and novices for Correct No-Go trials. FIG. 17E shows the results between experts and novices for Incorrect No-Go trials.

DETAILED DESCRIPTION

The disclosed subject matter provides methods and systems for evaluating a subject's response to a visual stimulus, such as a baseball pitch.

Figure 1:
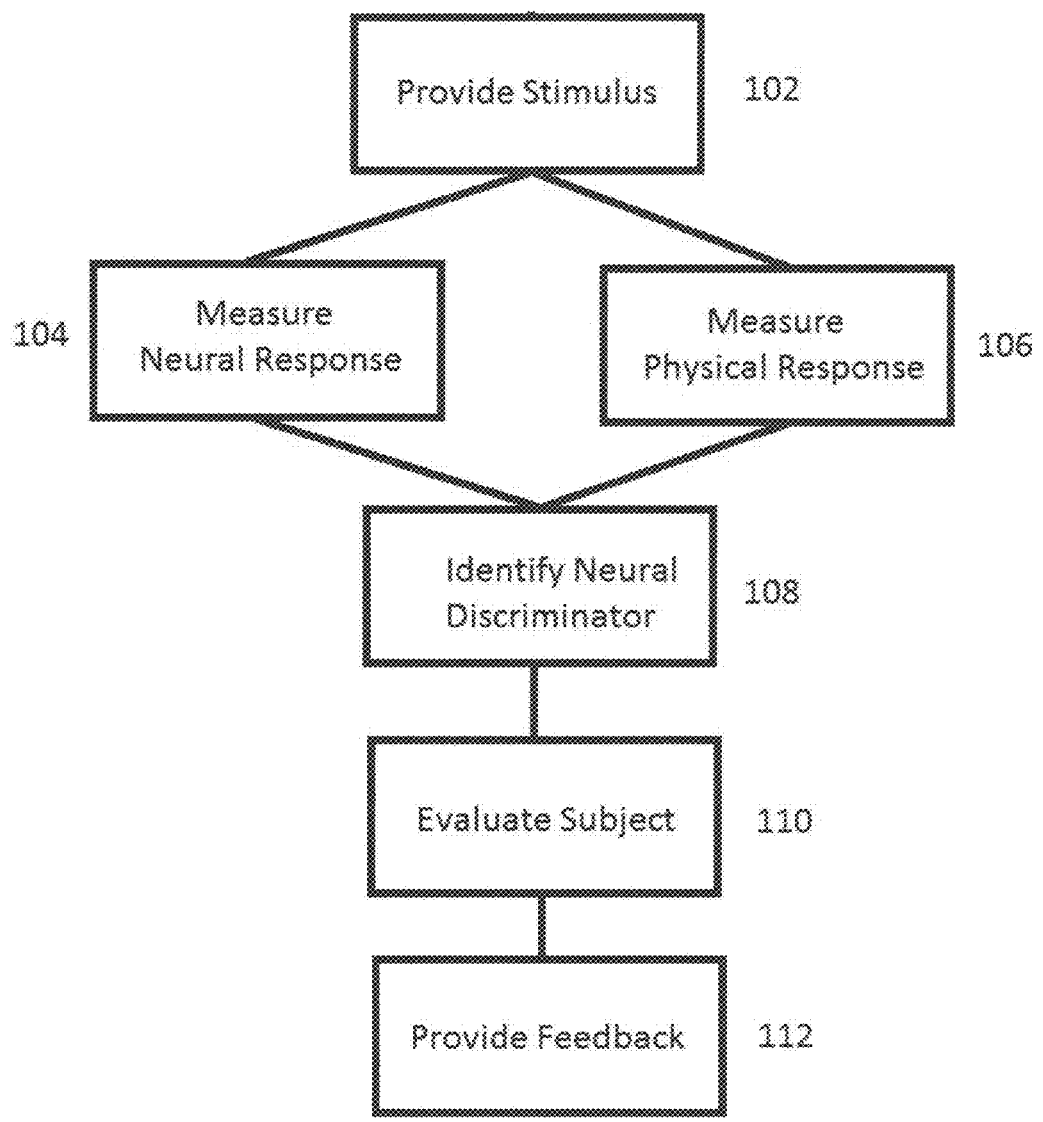
FIG. 1 is a flow chart illustrating an exemplary embodiment of a method for evaluating a subject's response when presented with a task related to a stimulus having a trajectory in accordance with the disclosed subject matter.

With reference to FIG. 1, a method for evaluating a subject's response to a visual stimulus in accordance with one embodiment of the disclosed subject matter is shown. A visual stimulus can be provided at 102. The visual stimulus can have a trajectory. Examples of visual stimuli having a trajectory include a baseball pitch, a cricket pitch, and a tennis serve. However, the disclosed subject matter is not limited to sports applications and can also be used in connection with any visual stimulus having a trajectory.

The visual stimulus can take many forms. For example, where the visual stimulus is a baseball pitch, the visual stimulus can be an actual baseball pitch. The visual stimulus can also be a recorded baseball pitch, e.g., one that is shown to a subject on a display screen after a processor retrieves the data related to the pitch from a storage device such as a hard drive or a flash drive. The visual stimulus can also be a simulated baseball pitch, e.g., one that is generated on a display screen based on solving equations or other data visualization techniques.

The visual stimulus can be related to a task. For example, where the visual stimulus is a baseball pitch, the task can be determining a type of pitch (e.g., fastball, curveball, or slider). In another embodiment of the disclosed subject matter, the task can be determining a final location of a pitch. For example, the task can be determining whether the pitch will land in a box defining the strike zone, or determining in which of several boxes the pitch will land.

With further reference to FIG. 1, a neural response of the subject can be measured at 104. The neural response can be measured using an electronic brain sensor such an electro-encephalography (EEG) sensor. The EEG data can be supplemented with data from a functional near infrared sensor or a functional magnetic resonance imaging sensor. The electronic sensor can be an array of brain activity sensors such as described in U.S. Pat. No. 7,835,787, which is incorporated herein by reference in its entirety for all purposes, although fewer sensors (e.g., between 10 and 63) can be used in the array. In accordance with an exemplary embodiment of the disclosed subject matter, the electronic brain sensor can be built into a batting helmet to allow the subject to face a live pitcher or pitching machine while monitoring the neural response.

Concurrently with the neural response, a physical response of the subject can be measured at 106. The physical response can be measured in any way known in the art. For example, where the visual stimulus is a baseball pitch, the subject can be instructed to press a button based on the type of pitch (e.g., fastball, slider, or curveball). In another embodiment, the physical response can be the subject swinging at a live pitch. In such an embodiment, the response can be measured by one or more sensors attached to or otherwise monitoring the bat used by the subject.

The test window for each trial can last from the start of the stimulus (e.g., when the pitcher's motion starts or when the ball first appears on the screen) to the end of the stimulus (e.g., after the ball has crossed home plate or disappears from the screen). Data before and after the start and end of the stimulus can also be recorded for purposes of calibration and baselining.

With further reference to FIG. 1, one or more neural discriminators can be identified at 108. An exemplary process for identifying one or more neural discriminators is described in U.S. Pat. No. 7,835,787, which is incorporated herein by reference in its entirety for all purposes.

Figure 2:
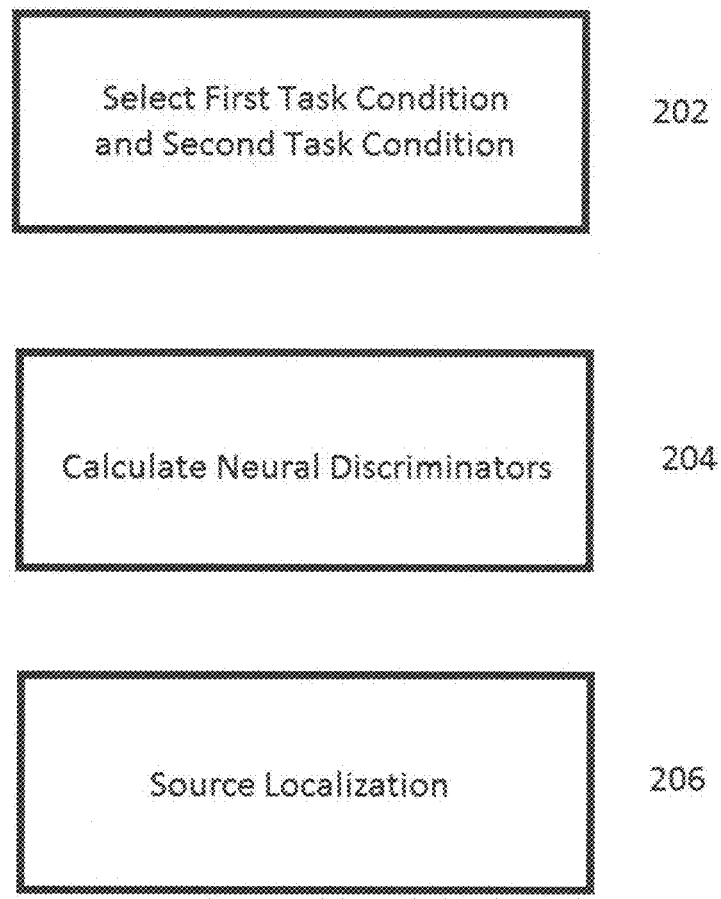
FIG. 2 is a flow chart illustrating an exemplary embodiment of a method for identifying a neural discriminator in accordance with the disclosed subject matter.

An exemplary embodiment of a process for identifying one or more neural discriminators in accordance with the disclosed subject matter is shown in FIG. 2. A first condition and a second condition can be selected in 202. The first condition and second condition are conditions associated with the task that can be distinguished. For example, the first condition can be a correct decision and the second condition can be an incorrect decision. For example, the first condition can be correctly identified fastballs and the second condition can be incorrectly identified fastballs. In another example, the first condition can be all correctly identified pitches and the second condition can be all incorrectly identified pitches.

In another example, the first condition can be a first correct decision and the second condition can be a second correct decision. For example, the first condition can be correctly identified fastballs and the second condition can be correctly identified curveballs. In another example, the first condition can be correctly identified fastballs and the second condition can be correctly identified pitches other than fastballs.

While the disclosed subject matter is generally described with respect to two task conditions, three or more task conditions can be used without departing from the scope of the disclosed subject matter. For example, the first task condition can be all fastballs, the second task condition can be all curveballs, and the third task condition can be all sliders. In another embodiment, the first task condition can be an incorrect response, a second condition can be a correct response, and a third task condition can be a late response (i.e., a response that is registered after some cutoff time, e.g., after the pitch has crossed home plate). In yet another embodiment, the first task condition can be all correctly identified fastballs, the second condition can be all correctly identified curveballs, the third condition can be all correctly identified sliders, the fourth condition can be all incorrectly identified fastballs, the fifth condition can be all incorrectly identified curveballs, and the sixth condition can be all incorrectly identified sliders.

The selection of the first and second conditions (or some larger number of conditions) will define the significance of the neural discriminator. The neural discriminator specifies the activity correlated with each condition, while minimizing activity correlated with both conditions.

One or more neural discriminators can then be calculated based on the selected two or more task conditions at 204. For example, the spatial distribution of the neural response data (e.g., EEG data) across a sensor array can be applied to a logistic regression model in order to learn an optimal linear discriminator. For example, in a sensor array having M values, and denoting x(t) as a vector of the M sensor values at time t, spatial weighing coefficients v can be computed such that:

$$y(t)=v^T x(t) \qquad (1)$$

is maximally discriminating between the times t, corresponding to two different task conditions. The sensor values x(t) can be measured over a temporal window having an onset time τ and has a duration δ. The onset time τ can be at the start of the visual stimulus or at an earlier time. The duration δ can be sufficient to cover the entire period of the visual stimulus, and can also cover a short time before and/or after the visual stimulus. For example, for simulated pitches, the temporal window can start when the stimulus appears on the screen and end when the stimulus disappears from the screen. Conventional logistic regression (Duda et al., Pattern Classification, John Wiley & Sons, 2nd Edition (2001), incorporated herein by reference in its entirety) can be used to find v.

A neural source associated with the one or more neural discriminators can be identified at 206. One method for localization of the one or more neural discriminators is described in U.S. Pat. No. 7,835,787, which is incorporated herein by reference for all purposes.

With further reference to FIG. 1, the subject's performance can then be evaluated at 110. In baseball, for example, earlier recognition of a pitch can be correlated with improved performance. Therefore, evaluating a subject can include determining how quickly the subject makes a decision, e.g., to determine what type of pitch is being delivered.

In accordance with another embodiment of the disclosed subject matter, evaluating a subject can include identifying and comparing physical reaction times, neural reaction times, spatial location information, and other information based at least in part on the neural discriminators. The neural discriminators and information based at least in part on the neural discriminator can further be combined with other statistics such as psychometric performance curves and consistency metrics.

The one or more neural discriminators, and data derived therefrom, can be compared to normative data. For example, repeated trials can identify particular characteristics of various types of hitters. The hitters can be classified as high school hitters, college hitters, minor league hitters, and major league hitters. Each category can further be broken down into poor, average, and good hitters. The subject's performance can then be categorized, either as a whole or by category (e.g., accuracy, neural reaction time, etc.) by category.

The subject's performance can also be evaluated over time. In accordance with one embodiment of the disclosed subject matter, the user's performance can be compared against one or more previous performances by the subject in order to determine whether the subject is improving. For example, the subject's neural and physical reaction time in a current trial can be compared to the subject's neural and physical reaction times in previous trials to determine, for example, whether the subject has increased the speed at which he/she can recognize the pitch (neural reaction time) and whether the subject has increased the speed at which he/she reacts to such recognition (the time between the neural response and the physical response).

The subject's performance can also be evaluated across difficulty levels. For example, the subject can be given a number of tasks with an increasing level of difficulty. In an exemplary embodiment, the subject can be given the task of identifying a pitch type (e.g., fastball, curveball, or slider) at different levels of pitch difficulty (based on speed, delivery motion, or other metrics). In accordance with another embodiment, the subject can be given the task of identifying a pitch type from an increasing list of choices. For example, the first task can be distinguishing between fastballs and sliders, the second task can be distinguishing between fastballs, sliders, and curveballs, and the third task can be distinguishing between fastballs, sliders, curveballs, and change-ups.

The task can also be varied in order to provide appropriate evaluation information. For example, batters generally attempt to anticipate what pitch a pitcher will throw. Some hitters are very good at this, which can result in improved neural response time. However, the ability to overcome an incorrect initial guess can also be important. In order to evaluate a subject's ability to overcome an initial incorrect guess, a subject can be primed before each pitch (i.e., they will be told that the upcoming pitch will be of a particular pitch type). In order to reinforce this, the majority of the pitches can be correctly identified in advance. However, a minority of the pitches can be incorrectly identified. By defining the task conditions as correctly primed pitches and incorrectly primed pitches, the subject's ability to overcome the initial incorrect guess can be evaluated. For example, a comparison between the neural reaction times for correctly primed pitches and incorrectly primed pitches can be used for purposes of such evaluation.

Figure 8:
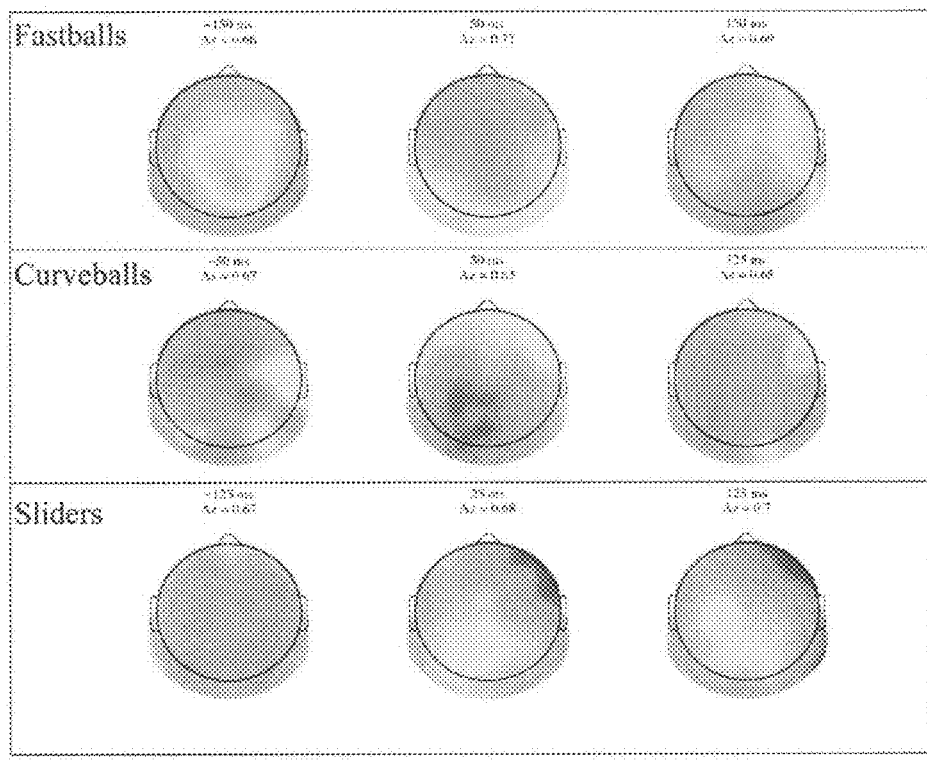
FIG. 8 illustrates scalp maps showing the group averaged stimulus-locked forward models comparing correctly-identified pitch types in accordance with an exemplary embodiment of the disclosed subject matter.

As part of the evaluation process, various visualization techniques can be used in presenting the neural discriminators or data derived therefrom. Such visualization techniques can include simple print-outs of data (e.g., neural reaction times and physical reaction times) or more advanced visualization techniques such as scalp maps (as shown in FIG. 9) or visualizations of the pitch (e.g., graphs showing the physical location of a pitch, as seen in FIG. 8). Other visualization techniques as known in the art, including those described herein, can also be used without departing from the scope of the disclosed subject matter.

The results of this evaluation can be used in a variety of ways. For example, the results can be taken into account when drafting or signing players. In another example, the evaluation of the subject can reveal that the subject has more problems, or takes a longer time, recognizing a first type of pitch (e.g., a curveball) than a second type of pitch (e.g., a slider). This information can be used to avoid putting the subject in a disadvantageous situation (e.g., a manager can choose not to use the subject against a pitcher that throws a lot of curveballs). Conversely, if the information is known to the opposing team, the opposing pitcher can utilize more curveballs than sliders in pitching to the subject.

With further reference to FIG. 1, the subject can be given feedback at 112. The feedback can assist the subject in improving performance.

In accordance with one embodiment of the disclosed subject matter, the feedback loop can provide information to the subject based on the subject's state prior to the visual stimulus. The temporal window can start before (e.g., several seconds to several milliseconds before) the visual stimulus is provided. The resulting neural discriminators can provide information on the best mental state for the subject prior to the visual stimulus. For example, where the subject is tasked with identifying a pitch type of a baseball pitch, neural response data can be measured over a temporal window starting several seconds prior to the pitch. Correctly identified pitches and incorrectly identified pitches can be selected as the two task conditions. The resulting neural discriminator can assist a subject in identifying the proper mental state for achieving the best results. The proper mental state can be identified using the logistic regression methods disclosed herein. In accordance with an exemplary embodiment of the disclosed subject matter, the raw data can be transformed from one signal domain to another via a time-frequency decomposition.

In accordance with another embodiment of the disclosed subject matter, the feedback loop can use additional data to provide feedback. For example, eye-tracking/pupilometry data can be used to provide feedback. Correct smooth pursuit eye movements can play a role in trajectory tracking. Eye tracking technology can compliment the neural discriminators and data derived therefrom in providing insights into subject performance. The resulting neural discriminator can assist a subject in identifying where his/her attention should be directed in order to achieve the best results.

Figure 3:
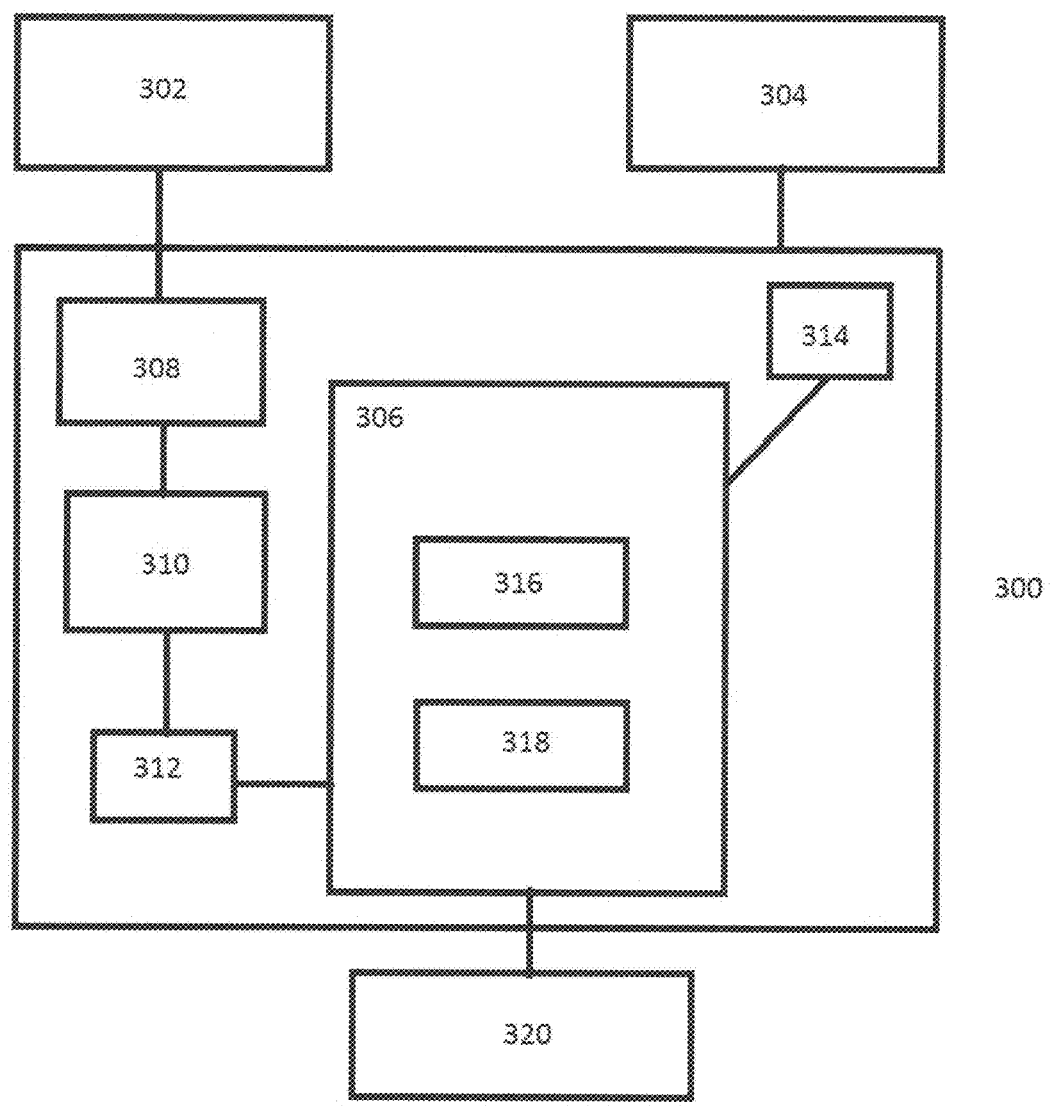
FIG. 3 illustrates an exemplary embodiment of a system for evaluating a subject's response when presented with a task related to a stimulus having a trajectory in accordance with the disclosed subject matter.

With reference to FIG. 3, a system for evaluating a subject's response to a visual stimulus in accordance with one embodiment of the disclosed subject matter is shown. The system 300 can include a brain activity sensor 302. The brain activity sensor 302 can be, for example, an EEG sensor. In accordance with one embodiment of the disclosed subject matter, the brain activity sensor 302 is built into a batting helmet. The brain activity sensor 302 can include electrodes such as Ag/AgCl electrodes. The number of electrodes can vary. For example, the brain activity sensor can include 128, 64, 32, or fewer than 20 electrodes. The brain activity sensor 302 can also include a like number of corresponding output channels. In FIG. 3, the brain activity sensor has 32 electrodes and 32 output channels.

The system 300 can also include a monitor 304, such as a CRT monitor, for displaying a recorded or simulated pitch to a subject.

The brain activity sensor 302 and the monitor 304 can be coupled to a processing system 306. The term "coupled," as used herein, refers to direct coupling, as through a wire or cable, or indirect coupling, as through wireless communication.

The processing system 306 can include a number of components. For example, the output of brain activity sensor 302 can be connected to an amplifier 308 and an analog-to-digital converter 310. The output of the analog-to-digital converter 310 can be stored in a non-transitory storage medium 312 such as a hard drive.

A portion of the brain activity sensor signal stored in the non-transitory storage medium 312 corresponding to the temporal window can be extracted from the storage medium 312 and provided to signal processor 314 which is coupled to the storage medium 312. The signal processor 314 can be configured to perform various signal processing methods, including identifying neural discriminators and localizing neural sources as described herein. The signal processor 314 can be a single processor, or can include two or more processors. Each of the two or more processors can perform one or more steps of the signal processing methods disclosed herein. For example, signal processor 314 can include a neural discriminator identification processor 316 and a source localization processor 318. Neural discriminator identification processor 316 and source localization processor 318 can be separate hardware components, or they can be a single processor designed or programmed to carry out both tasks.

The signal processor 314 includes at least one processor, i.e., at least one electric circuit. The signal processor 314 can be hardware only, or can be a combination of hardware and software. In embodiments where the signal processor 314 includes software and hardware, a non-transitory storage medium 316 can include instructions that, when implemented, cause the processor to perform the signal processing methods described herein. The non-transitory storage medium 316 can include a hard drive or removable storage media such as compact discs or other optical storage media and flash drives.

The signal processor 314 can be coupled to an output device 320 for presenting the resulting data to a user of the system. The output device 320 can be, for example, a printer for providing the results on a printed page. In accordance with another embodiment of the disclosed subject matter, the output device can be a display screen.

The system 300 can also include additional components for effecting the methods disclosed herein. For example, in accordance with one embodiment of the disclosed subject matter the system 300 can include eye-tracking sensors.

As described above in connection with certain embodiments, a processing system 306 is provided to identify neural discriminators and perform additional functions as disclosed herein, and to generate neural discriminators and data derived therefrom used by output devices 320 for more effectively evaluating the performance of the subject. In these embodiments, the processing system 306, such as a computer, plays a significant role in permitting the system to provide information for evaluating a subject's response to a task associated with a stimulus having a trajectory. For example, the presence of the computer allows the neural discriminators or data derived therefrom to be output (e.g., on a display screen in the form of an image), and can further allow for the provision of feedback to the subject.

Example 1

Six subjects were chosen for participation in this example (1 female, mean age—27.33 years). None of the subjects had professional or collegiate baseball experience. All subjects reported normal or corrected vision and no history of neurological problems.

For the visual stimulus, subjects viewed 12 blocks of 50 simulated baseball pitches with a mean jittered inter-stimulus interval of 2150 ms on a computer screen. The simulated view was that of where the catcher would sit on a standard baseball diamond, i.e., at the end point of the pitch trajectory. From a library of fifty pitches, each coming from one of three pitches types ("fastballs," "curveballs," and "sliders"), the subject was presented, on each trial, a pitch chosen at pseudorandom.

The subjects were instructed to identify the type of pitch as quickly as possible via a keyboard button response, where each pitch choice was mapped to a unique button ("j", "k", or "l"). Subjects were told to respond while the ball is still on the screen. All button responses were executed with the right hand, regardless of handedness. In an initial training phase, subjects learned the general trajectory of each pitch by viewing examples, and for a short practice session they responded with the button response. The practice session contained 20 pitches selected at pseudorandom with no feedback and subject were asked afterwards if they felt comfortable doing the task in the amount of time needed. All subjects responded in the affirmative and the 12 blocks of 50 pitches began with EEG data being recorded. Participants did not receive feedback or collect a reward for their performance; however, they did receive compensation for their time.

A Dell Precision 530 Workstation was used to present the visual stimuli with E-Prime 2.0 (Sharpsburg, Pa.). The subjects sat in an RF-shielded room 100 cm from the center of the computer screen, where the stimulus display area covered a horizontal angle of ±6.5° and a vertical angle of ±5.0°.

The start of each pitch was the stimulus event by which the EEG time-locking occurred. Stimulus events were passed to the EEG recording system through a TTL pulse in the event channel. In post-hoc analysis, response events were synchronized to the EEG via their latencies from the stimulus event.

Each pitch video clip was created using a differential equation solver in Matlab 2010a (Mathworks, Natick, Mass., USA). and exported to an audio-video Interleaved (.avi) movie file sampled at 60 Hz (refresh rate of display monitor). Most baseball pitches can be simulated using 6-coupled differential equations.

$$\frac{\partial x}{\partial t} = v_x \tag{2}$$

$$\frac{\partial y}{\partial t} = v_y \tag{3}$$

$$\frac{\partial z}{\partial t} = v_z \tag{4}$$

$$\frac{\partial v_x}{\partial t} = -F(v)vv_x + B\omega(v_z\sin\phi - v_y\cos\phi) \tag{5}$$

$$\frac{\partial v_y}{\partial t} = -F(v)vv_y + B\omega v_x\cos\phi \tag{6}$$

$$\frac{\partial v_z}{\partial t} = -g - F(v)vv_z - B\omega v_x\sin\phi \tag{7}$$

$$F(v) = 0.0039 + \frac{0.0058}{1 + e^{(v-v_d)/\Delta}} \tag{8}$$

The first three equations (Equations 2-4) specify the change in spatial location in each direction, which equals the velocity of the baseball. The last three equations specify the accelerations due to the drag (F(v)), the Magnus force (B), and gravity (g) acting on the baseball. Equation 8 can be used to calculate the drag force at different velocities with $v_d$=35 m/s and $\Delta$=5 m/s. The Magnus force (b), which occurs due to differential drag on a spinning object, is approximated here to be $4.1\times10^{-4}$ (dimensionless). After specifying the initial conditions ($x_0$, $y_0$, $z_0$, $v_{x0}$, $v_{y0}$, $v_{z0}$, $\omega$ (rotational frequency)), the 6 ordinary differential equations were solved in MATLAB.

The three pitches—fastball, curveball, and slider—have well-defined individual initial conditions. To create each pitch, only the initial velocity and the rotation angle were be varied. For each pitch class, 50 pitches were created by randomly sampling distributions of initial conditions for velocity, rotation angle, launch angle, and horizontal launch angle. The values and distributions for each pitch class are specified in Table 1.

TABLE 1

|  | Initial Velocity | Rotation Angle | Vertical Launch Angle | Horizontal Launch Angle | Rotational Frequency | Duration |
|---|---|---|---|---|---|---|
| Fastball | 83 ± 3 MPH | 270 ± 3° | 0.5 ± 0.3° | 0.7 ± 0.3° | 1800 rpm | .53 ± .01 s |
| Curveball | 70 ± 3 MPH | 50 ± 10° | 1.7 ± 0.3° | 0.7 ± 0.3° | 1800 rpm | .64 ± .02 s |
| Slider | 75 ± 3 MPH | 0 ± 5° | 1.7 ± 0.3° | 0.7 ± 0.3° | 1800 rpm | .59 ± .02 s |

For each simulated pitch, a blue circle was plotted on a gray grid for every frame of the trajectory. The size of the blue circle increased as it approached the viewer, so as to give the illusion of depth. When the ball crossed "home plate," the blue circle disappeared. The frames were compressed into a .avi movie format for each pitch simulation. The trajectories, for each simulation, were saved in a separate file for later use.

EEG data was acquired in an electrostatically shielded room ETS-Lindgren, Glendale Heights, Ill., USA) using a BioSemi Active Two AD Box ADC-12 (BioSemi, The Netherlands) amplifier from 64 scalp electrodes. Data were sampled at 2048 Hz. A software-based 0.5 Hz high pass filter was used to remove DC drifts and 60 and 120 Hz (harmonic) notch filters were applied to minimize line noise artifacts. These filters were designed to be linear-phase to minimize delay distortions. Stimulus events—i.e., pitch-movie start times and pitch types—were recorded on separate channels.

Independent components analysis (ICA) was run using EEGLAB to remove eye-blink artifacts. In stimulus-locked epoching (−1000 ms to 1500 ms), the average baseline was removed using data from −1000 ms to 0 ms. After epoching to stimulus events, an automatic artifact epoch rejection from EEGLAB was run to remove all epochs that exceeded a probability threshold of 5 standard deviations from the average. Similarly, in response-locked epoching, the average baseline was removed from −1500 ms to −500 ms ad the same automatic artifact epoch was run.

A single-trial analysis of the filtered, epoched, and artifact-removed EEG was performed to discriminate between a set of stimulus or response conditions. First, only behaviorally-correct pitches wee considered, and a classifier was trained to classify a given pitch (e.g., a fastball) vs. pitches of other classes (e.g., curveball and slider). Second, behaviorally correct versus behaviorally incorrect pitches were classified within each pitch class (e.g., correctly identified fastballs versus incorrectly identified fastballs). A summary of the classification analysis is shown in Table 2.

TABLE 2

| Correct Pitches | | Correct-Incorrect | |
|---|---|---|---|
| Class 1 | Class 2 | Class 1 | Class 2 |
| Fastball | Not-Fastball | Correct Fastball | Incorrect Fastball |
| Curveball | Not-Curveball | Correct Curveball | Incorrect Curveball |
| Slider | Not-Slider | Correct Slider | Incorrect Slider |

Logistic regression was used as a classifier to find optimal projection for discriminating between the two chosen conditions over a specific temporal window. Specifically, a training window was defined starting at either a pre-stimulus or post-stimulus onset time $\tau$, with a duration of $\delta$, and used logistic regression to estimate a spatial weighting vector $\vec{w}_{\tau,\delta}^T$ which maximally discriminates between EEG sensor array signals X for each class (e.g., fastballs versus not-fastballs):

$$\vec{y} = \vec{w}_{\tau,\delta}^T X \quad (9)$$

In Equation 9, X is a N×T matrix (N sensors and T time samples). The result is a "discriminating component" $\vec{y}$ that is specific to activity correlated with each condition, while minimizing activity correlated with both task conditions. The term component is used instead of source to make it clear that this is a projection of all activity correlated with the underlying source. For the experiments, the duration of the training window $\delta$ was 50 ms and the center of the window $\tau$ was varied across time $\tau \in 0$, 1000 ms in 25 ms steps for stimulus-locked, and was varied across time $\tau \in -575$, 575 ms in 25 ms steps for response-locked. The re-weighted least squares algorithm was used to learn the optimal discriminating spatial weighting vector $\vec{w}_{\tau,\delta}^T$.

In order to provide a functional neuroatomical interpretation of the resultant discriminating activity, and due to the linearity of the model, the electrical coupling coefficients were calculated as:

$$\vec{a} = \frac{X\vec{y}}{\vec{y} \cdot \vec{y}} \quad (10)$$

The equation describes the electrical coupling coefficient $\vec{a}$ of the discriminating component $\vec{y}$ that explains most of the activity X.

The performance of the linear discriminator was quantified by the area under the receiver operator characteristics (ROC) curve, referred to here as $A_z$, using a leave-one-out procedure. The ROC $A_z$ metric can be used to characterize the discrimination performance as a function of sliding our training window from 0 ms pre-stimulus to 1000 ms post-stimulus (e.g., by varying $\tau$) for stimulus-locked and −575 ms pre-response to 575 ms post-response for the response-locked. These time periods provided substantial time both after the stimulus and behavioral response (button press) to observe any electrophysiological response to the pitch.

The statistic significance of $A_z$ was quantified in each window $\tau$ using a relabeling procedure. With 41 windows for stimulus-locked and 47 for response-locked, it was necessary to correct for this number of comparisons with stimulus- and response-locked leave-one-out respectively. To have a Bonferroni corrected p<0.05 threshold in both locking conditions, enough permutations were run to have a suitable number of samples within the p<0.001 threshold (i.e., p<0.05/41 and p<0.05/47). To this end, the truth labels (e.g., pitch was a fastball, curveball, or slider) were randomized for each trial and the classifier was retrained. This was done 3750 times for each subject (1250 permutations for each pitch comparison combination), giving a total of 22500 permutations for a group level analysis. The $A_z$ values from these permutations were used to establish a p<0.001 threshold, i.e., a P<0.05 corrected for multiple comparisons.

Source localization was also used to investigate the differences between correctly versus incorrectly identified pitches. First, the stimulus-locked EEG data of incorrectly versus correctly identified pitches was classified, as summarized in FIG. 4A. This was done on a subject-specific basis, except for one subject for whom there were no errors in discriminating the slider; therefore, that subject was removed so as not to bias the results. For each of the remaining five subjects, the window at which the LOO $A_z$ value was maximized was selected, with the constraint that the subject specific maximum was not outside the range of three standard errors of the pitch-specific mean peak timing. This was done to ensure that the localization analysis was investigating a temporally common phenomenon across subjects.

Using these markers in time, the EEG sensor data was trial-averaged across all epochs that were either correctly identified or incorrectly identified, creating a grand average ERP for each of the five subjects, for each pitch and across both accuracies. Given five subjects, three pitches, and two conditions, this results in a total of fifteen ERPs for each condition (i.e., for correctly identified and incorrectly identified pitches).

Using these grand average ERP values, a source localization algorithm was used to estimate the most likely cortical source distributions. The algorithm solves for the most likely current source distribution in the cortex based on EEG sensor data and array topology. These distributions were used to compare the incorrect versus correct classification conditions across subjects and pitches.

Figure 4A:
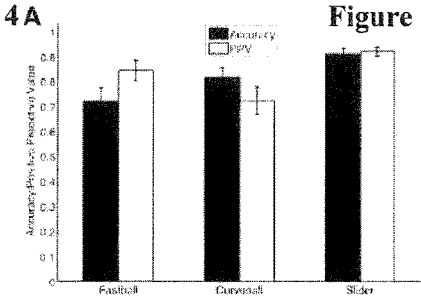
FIG. 4A-4B illustrates mean behavioral response times measured in accordance with one embodiment of the disclosed subject matter.
Figure 4B:
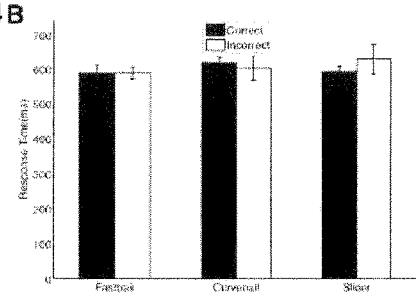

As shown in FIG. 4A-4B, the mean accuracy was 72%, 82%, and 91% for fastballs, curveballs, and sliders, respectively. The positive predictive value—i.e., the number of true positives divided by the sum of true positives and false positives for each pitch class—was also calculated. The PPV of each pitch class showed that the subjects were confident when selecting sliders and fastballs, however, for curveballs, the PPV is significantly less that the accuracy, indicating that the curveball can be the default choice for the subjects—i.e., it was often selected as a false positive.

Mean reaction times, for correctly and incorrectly identified pitches, are graphed in FIG. 4B. Due to the time constraints imposed by the paradigm, there is no difference in mean response times between correctly and incorrectly identified pitches (p=0.9573—Fastball, p=0.5233—Curveball, p=0.3350—Slider, Student's Paired t-test). Mean response times for correctly identified pitches were 590 ms, 618 ms, and 594 ms for fastballs, curveballs, and sliders, respectively).

The behavioral results, which are shown in FIG. 5A, show responses times as a probability density function with truncations on the right-side of the distributions, indicating the threshold enforced 100 ms after the pitch arrived at the plate. Mean response times for correctly identified pitches were 590 ms, 618 ms, and 594 ms for fastballs, curveballs, and sliders, respectively. The first peaks of each pitch's response distribution are at 494 ms (fastballs), 558 ms (sliders), and 590 ms (curveballs).

To test whether the response times were significantly different from each other, a 3-way ANOVA was run with the three factors being subject, pitch type, and correct/incorrect classification. The subject factor was treated as a random effect while the other two factors were treated as fixed effects in the model. No significant differences were found in all of the comparisons tested (p>0.05)—difference between pitch types (p=0.08, F=3.38, df=2), difference between correct/incorrect (p=0.68, F=10.6, df=5), the interactions between pitch type and correct/incorrect (p=0.24, F=1.66, df=10). The ANOVA indicates that the mean behavioral responses are not statistically different regardless of the pitch type of whether the subject classified the pitch correctly.

FIG. 5B shows the mean discrimination performance ($A_z$ values) across all subjects and for each pitch using stimulus-locked EEG discrimination. From the stimulus-locked analysis, a relationship between the speed of the pitch and the timing of peaks in both neural and behavioral data can be seen. In FIG. 5B the correctly identified fastballs exhibit the earliest significant EEG discrimination (300 ms), while sliders (425 ms) and curveballs (500 ms) follow. As expected, the sequence of these peaks follows the relative speed of these pitches, i.e., fastballs, sliders, and then curveballs. Comparing these peaks to the behavioral results of FIG. 5A, each of the response distribution peaks immediately followed the relative timing of each pitch's first significant neural discrimination.

As the response times show, the stimulus-locked discrimination overlaps the responses ~420-720 ms, making it difficult to isolate non-motor elements in the signal during these time periods. However, after the responses, the highest peaks of discrimination for each pitch are seen (750 ms for fastballs, 700 ms for sliders, and 850 ms for curveballs). To test whether these post response peaks are due to the differences in the response time distributions, a separate analysis was run on a subset of the data where the RT distributions were matched between classes. These large peaks remain and are therefore can indicate a post-response evaluative process specific to identifying each pitch correctly.

Figure 6:
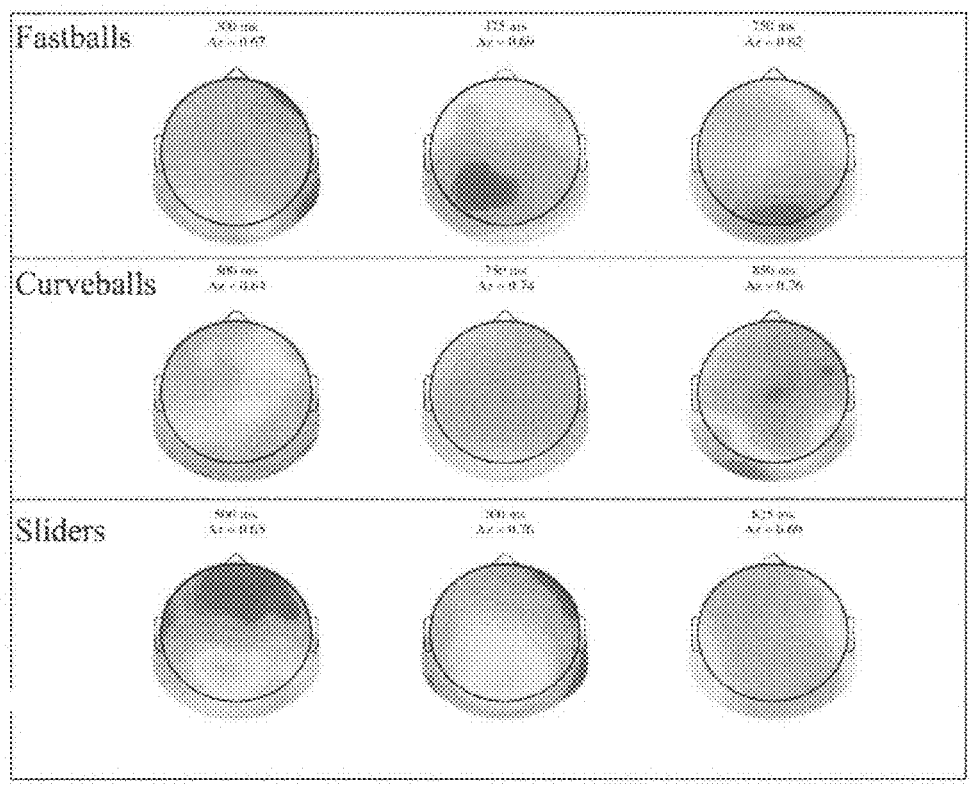
FIG. 6 illustrates scalp maps showing the group averaged stimulus-locked forward models comparing correctly-identified versus incorrectly-identified pitches in accordance with an exemplary embodiment of the disclosed subject matter.

Group mean stimulus-locked forward models, shown as scalp plots, are given in FIG. 6. Plots are for selected time points across all three pitches, where the center of the discrimination window is indicated at the top of each subfigure. Dark red and blue colors indicate strong discriminator power from electrodes in that region. While the areas of discrimination change over time for each pitch type, discrimination power is consistently located in the posterior and occipital portions of the scalp plots.

Figure 7:
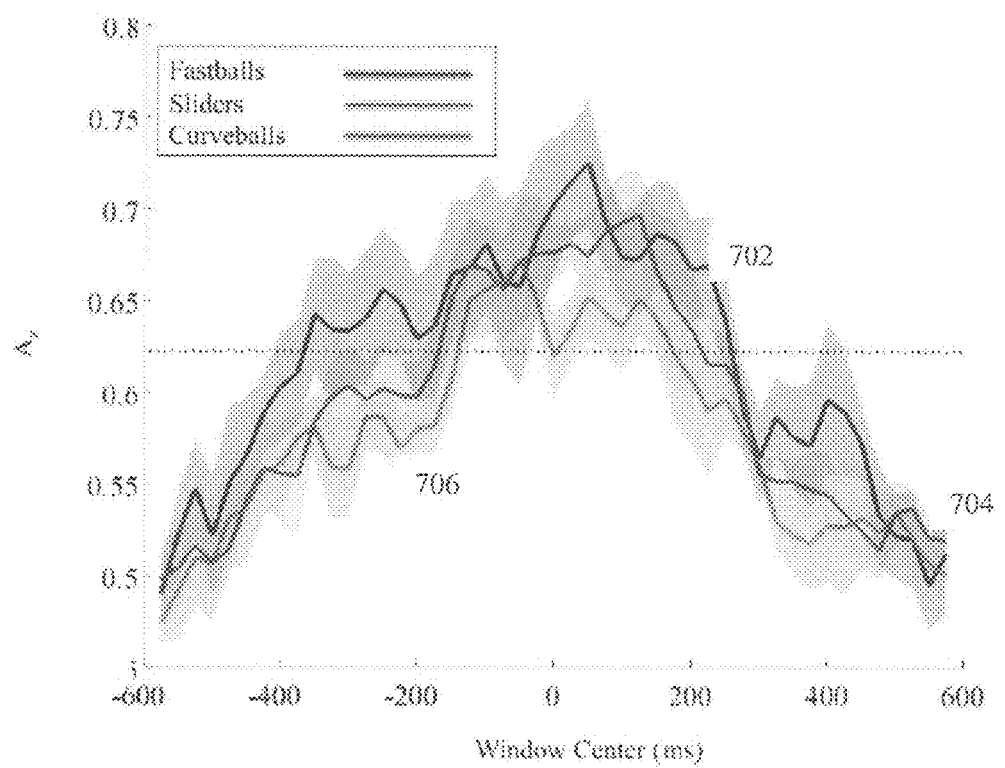
FIG. 7 illustrates group mean and standard error bands for response-locked leave-one-out EEG discrimination performance in accordance with an exemplary embodiment of the disclosed subject matter. Fastballs are plotted at 702, sliders are plotted at 704, and curveballs are plotted at 706.

Due to the potential of a motor confound in the neural signal, EEG data locked to the response times is also classified as shown in FIG. 7. Once again, using correctly identified pitches, the $A_z$ values were calculated across all subjects and for each pitch.

In line with stimulus-locked responses, significant pre-response peaks (Bonferroni corrected, p=0.05) are found for each pitch that follow the relative speeds of each pitch. In particular, the mean pre-response peak for fastballs (−350 ms) precedes that of sliders (−125 ms) and then curveballs (−50 ms). As with the stimulus-locked discrimination, there is a post-response period in which the mean discrimination is as high or higher than it was pre-response for each pitch (fastballs at +50 ms, sliders at +125 ms and curveballs at +50 ms and +125 ms), indicating a potential post-response evaluating of the evidence gathering and subsequent decision.

Similar to the stimulus locked figure, mean response-locked forward model scalp plots are shown in FIG. 8. Again, it can be seen that discrimination power is located in the posterior of the brain and the spatial distributions change over time. Only the slider post-response scalp map shows a pattern that can be indicative of a button response (125 ms window shows lateralized contralateral discriminatory activity—i.e., left side activity indicative of a right handed button press).

Figures 9A, 9B:
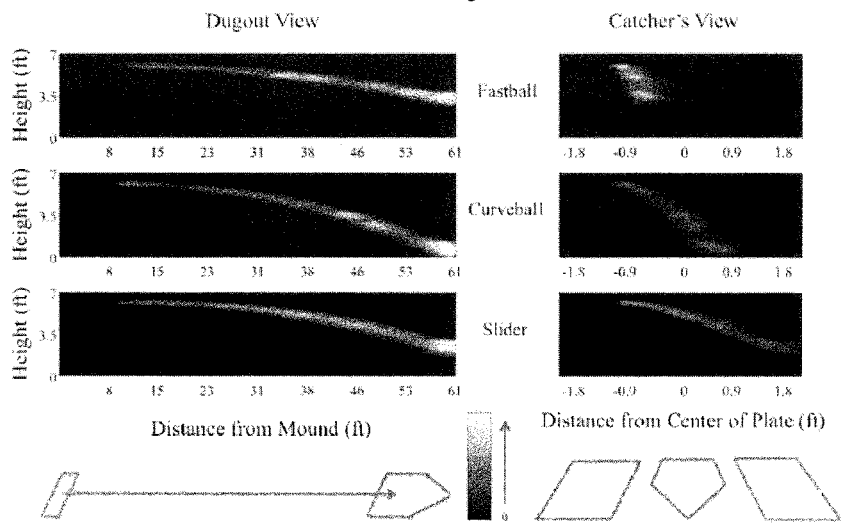
FIG. 9A-9B illustrates spatial distributions of single-trial peak discrimination in accordance with an exemplary embodiment of the disclosed subject matter.

Using the stimulus-locked single-trial analysis, spatial distributions of the neural markers were constructed across trials and compared these distributions across pitch types. Specifically, the spatial positions of the maximum y value for $\tau \in [0, \tau_{plate}]$ was computed, where $\tau_{plate}$ is the time at which the pitch reaches the end of its trajectory, i.e., at home plate. Doing this analysis across all subjects, and for each pitch, a "heat map" representation of the probability density function of the spatial position in the pitch trajectory having the most discriminating neural component was created. FIG. 9A-9B shows these distributions for both a side view of the trajectory (i.e., the "dugout view") and a heads-on view (i.e., the "catcher's view"). Features of the baseball diamond, such as the pitcher's rubber, home plate and the batter's boxes, have been added (not to scale) for a frame of reference.

Both views provide insight into the amount of evidence (e.g. time integration and spatial information) required to classify each pitch. From FIG. 9A, it is seen that common to all pitches is peak discrimination happening when the ball arrives at the plate, likely a result of the tight coupling of the decision with the motor response. However, there are differences between these distributions if the probabilities are considered prior to when the ball reaches the plate. For example, the fastball has discrimination peaks from mid-trajectory to home plate. The slider also shows this trend, though the probability mass is spread more throughout the trajectory and is thus less localized in terms of pitch position. Finally, the curveball (i.e., the slowest pitch) shows local peaks in the spatial distribution in the later half of the trajectory, presumably due to the slower seed of this pitch relative to the fastball and slider.

Similarly, the catcher's view (FIG. 9B) shows peak discrimination early in the fastball's trajectory, whereas both the slider and the curveball exhibit distributions spread across the entire trajectory of the pitch. Together, these plots indicate that, due to the higher relative speed and distinct trajectory of the fastball compared to the curveball and slider, the decision process resulting in a correct identification of the fastball occurs earlier in the spatial trajectory than it does for the sliders and curveballs, both of which take incrementally longer periods of time to arrive at the plate.

With further reference to FIG. 4A-4B, not all pitches were correctly classified by the subjects. Correct versus incorrect pitch classification was therefore analyzed in terms of the EEG discriminating components. Using the temporal windows having maximum $A_z$ within ach subject and pitch combination, pitch specific common windows were found covering 570±89 ms, 744±69 ms, and 522±96 ms for fastballs, curveballs, and sliders, respectively. For only two of the fifteen combinations of three pitches and five subjects, maximum $A_z$ values were found that exceeded three standard errors from the mean. For those two cases, the second maximum peak in $A_z$ from the next concave down region in the epoch was chosen. These points turned out to be within three standard errors of mean. Thus all analysis was in a temporal period that can be considered as "common decision processing" at a group level.

Figure 10:
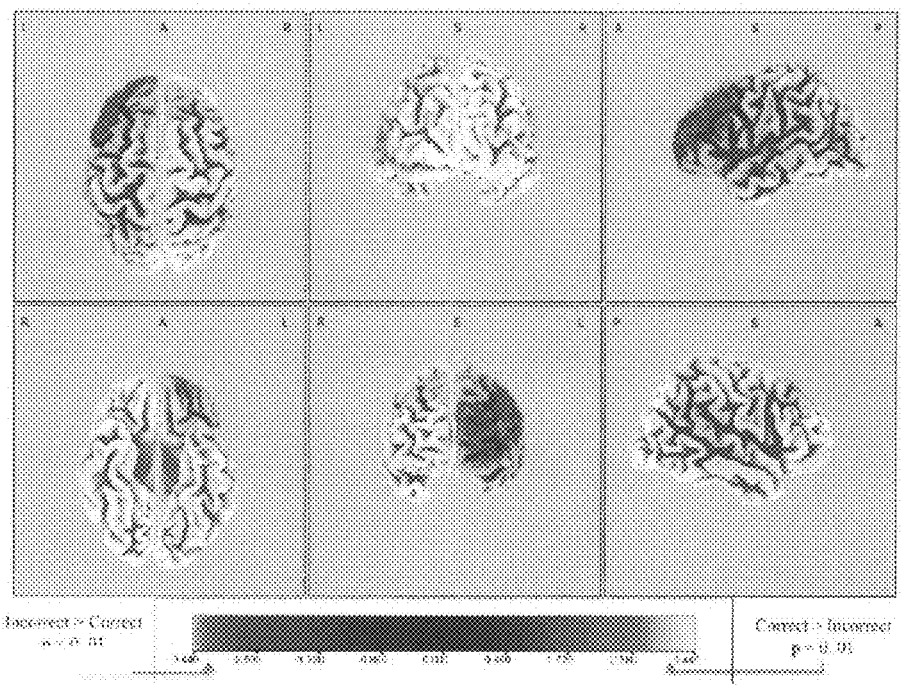
FIG. 10 illustrates source distributions identified using a paired t-test for correct versus incorrect identification distributions in accordance with an exemplary embodiment of the disclosed subject matter.

EEG data was extracted from these windows and solved for the source distribution using sLoreta. A paired t-test was performed for correct vs. incorrect identification distributions, with the resulting t-distribution of the log of the F-ratio (F(1, 13)) shown in FIG. 10. 5000 permutations were used to establish significance levels (p<0.01) for the null hypothesis of no difference in activity between incorrectly identified and correctly identified pitches. Though the hypothesis of correctly identified pitches shows no significant similarities, that of incorrectly identified pitches shows a common neuronal current source located in the left frontal cortex showing peaks in Brodmann Area 10 (BA 10, MNI (−35, 55, 20)). This result indicates left-lateralized common neuronal activity when subjects incorrectly identify the pitch, i.e., when they "miss." This result is invariant to the type of pitch, given that all pitches were considered in this analysis.

Example 2

Six subjects were chosen for participation in this example (1 female, mean age—27.33 years). None of the subjects had professional or collegiate baseball experience. All subjects reported normal or corrected vision and no history of neurological problems.

Nineteen subjects were chosen for participation in this example: 9 collegiate Division I baseball players (mean age—19.9±1.1 yrs) and 10 non-player novices (mean age—21.2±1.6 yrs). None of the novice subjects had any collegiate baseball experience. All of the expert baseball players were active players on a collegiate baseball team. All subjects reported normal or corrected vision and no history of neurological problems. All novices were right handed, while one of the baseball players was left-handed.

Each pitch was simulated via a differential equation solver in Matlab 2010a (Mathworks, Natick, Mass., USA) and presented these using PsychToolbox (Brainard, 1997). Pitches were simulated using the differential equations (2) through (7) above.

After specifying the initial conditions (x0, y0, z0, vx0, vy0, vz0, ω(rotational frequency)), the 6 ordinary differential equations (2) through (7) were solved in MATLAB. Each of the three pitches—fastball, curveball, and slider—has well-defined initial conditions. To create each pitch, the initial velocity and the rotation angle were varied. All initial velocities were sampled from the same uniform distribution (78±3 mph), though each pitch had its own rotation angle distribution (Fastball (270°+5°), Curveball (50°+5°), Slider (0°+5°)). For each simulated pitch, an isoluminant green circle was plotted on a gray background for every frame of the trajectory. The size of the circle increased as it approached the viewer, so as to give the illusion of depth. When the ball crossed "home plate", the circle disappeared.

Subjects viewed 5 blocks of 90 simulated baseball pitch trials on a computer monitor with a jittered inter-stimulus interval (ISI) of mean=3 s, SE=225 ms. Subjects sat at a distance of 51" from the screen. The simulated view was that of the catcher sitting on a standard baseball diamond, i.e. at the end point of the pitch trajectory (horizontal view 3.93°, vertical view 1.12°). The subject was presented with a pitch chosen at pseudorandom ("fastballs", "curveballs", and "sliders"), where the initial conditions of the trajectory were also jittered so that no two pitches from the same category followed the exact same trajectory. We used these stimuli to create a Go/No-Go paradigm. Preceding the pitch, a horizontal bar (S1) (horizontal view 3.93°, vertical view 0.28°) appeared onscreen for 950 ms, during which time the horizontal length of the bar shrunk at a constant rate until it disappeared. The bar shrank from either left to right, or vice versa, with equal pseudorandom uniform probability. While the bar was onscreen, a single-letter cue indicated above it the possible pitch trajectory to follow ('F' for fastball, 'C' for curveball, or 'S' for slider; horizontal view 0.28°, vertical view 0.28°). Once the bar shrank completely in length, the pitch trajectory (S2) began from that point on the screen.

Subjects were instructed to press a button on a keyboard only if the trajectory cue matched the actual pitch trajectory. For instance, if the cue above the horizontal bar was a 'F' and a fastball trajectory followed, then the subject would be expected to execute a button response (i.e., a 'Go'). If a curveball or slider trajectory were to follow the same cue, then the subject would be expected to refrain from executing a button response (i.e., a 'No-Go'). For this experiment, 60% of trials were 'Go' trials and 40% were 'No-Go' trials in order to control for the oddball effect in a more standard Go/No-Go paradigm. Subjects were told they must respond while the ball was still on the screen. Visual feedback was presented after the trajectory's completion in the form of a cross ('+') for correct responses and dash ('−') for incorrect responses. A 'Go' response was not considered correct unless the cue matched the trajectory and the button response occurred before the end of the trajectory (i.e. before the simulated ball disappeared from the screen). All button responses were right handed using the index finger, regardless of subject's handedness. Subjects were instructed to respond, "as fast and as accurately as possible." Subjects performed an initial training and practice phase where they had to score an accuracy of at least 60%. After subjects reached this performance, recording EEG for 5 blocks of the experiment began.

EEG data was acquired in an electrostatically shielded room (ETS-Lindgren, Glendale Heights, Ill., USA) using a BioSemi Active Two AD Box ADC-12 (BioSemi, The Netherlands) amplifier from 64 Ag/AgCl scalp electrodes arranged in the 10-20 System. Data were sampled at 2048 Hz. A software-based 0.5 Hz high pass filter was used to remove DC drifts, a 60 Hz (harmonic) notch filter to minimize line noise artifacts, and a 100 Hz low pass filter were applied before resampling the data to 256 Hz. These filters were designed to be linear-phase to minimize delay distortions. Stimulus events—i.e., countdown, pitch type, responses—were recorded on separate channels.

Independent components analysis (ICA) was run using EEGLAB (Delorme and Makeig, 2004) and the FastICA (Hyvarinen, 1999) algorithm was used to remove eye-blink artifacts. Data were then re-referenced to the average across all electrodes. In S2 stimulus-locked epoching (−1500 ms to 2000 ms), the average baseline was removed using data from −200 ms to 0 ms. After epoching to stimulus events, an automatic artifact epoch rejection algorithm from EEGLAB was run to remove all epochs that exceeded a probability threshold of 5 standard deviations from the average. Trials where the subject's RT was earlier than 100 ms from pitch onset were excluded from further analysis.

Percent error rates and RTs were analyzed. Errors were broken down into both omissions and commissions, i.e., no-responses and late responses in Go trials, and button presses in No-Go trials. Repeated-measures ANOVAs on each behavioral measure were carried out using Trial type (two levels: Go, No-Go) as the within-subject factor and group (expert/novice) as the between subject factor. Post hoc comparisons were also made in order to determine the significance of contrasts by applying the Bonferroni procedure (alpha=0.05).

A traditional ERP analysis was performed on the filtered, epoched, and artifact-removed EEG. The analysis focused on a single-trial approach to discriminate between a set of stimulus or response conditions. First, only behaviorally correct trials were considered. Regularized logistic regression was used as a classifier to find an optimal projection for discriminating between behaviorally correct Go and behaviorally correct No-Go trials over a specific temporal window. Specifically, a training window starting at either a pre-stimulus or post-stimulus onset time $\tau$, with a duration of $\delta$, was defined, and logistic regression was used to estimate a spatial weighting vector that maximally discriminates between EEG sensor array signals X for each class (e.g., Go vs. No-Go trials), as shown in Equation (9) above. X is an N×T matrix (N sensors and T time samples). The result is a 'discriminating component' that is specific to activity correlated with each condition, while minimizing activity correlated with both task conditions. The duration of the training window ($\delta$) was 50 ms and the center of the window ($\tau$) was varied across time in 25 ms steps. The re-weighted least squares algorithm was used to learn the optimal discriminating spatial weighting vector. The electrical coupling coefficients was estimated as:

$$\vec{a} = Xy^T(yy^T)^{-1} \qquad (11)$$

This equation describes the electrical coupling of the discriminating component that explains most of the sensor activity. The performance of the linear discriminator was quantified by the area under the receiver operator characteristic (ROC) curve, referred to here as AUC, using a leave-one-out procedure. The ROC AUC metric was used to characterize the discrimination performance as a function of sliding the training window from 0 ms pre-stimulus to 1000 ms post-stimulus (i.e, varying $\tau$).

The statistical significance of AUC in each window ($\tau$) was quantified using a label permutation procedure. Specifically, the truth labels (i.e. trial was a Correct Go or a Correct No-Go) were randomized for each trial and the classifier was retrained. This was done 1000 times for each subject at the 500 ms window, giving a total of 19000 permutations. The AUC values from these permutations were used to establish a p-value for the mean AUC at each time window. Control for multiple comparisons was performed using a Bonferroni correction at p<0.05. All significant results are thus reported at p<0.05 corrected for multiple comparisons.

Source localization (sLoreta) (Pascual-Marqui, et al., 1999) was used to estimate the most likely cortical source distributions that differentiated experts from novices for Correct Go, Correct No-Go, and Incorrect No-Go trials. Specially, on a subject-by-subject basis, the window was selected at which the LOO AUC value was maximum for the Correct Go versus Correct No-Go comparison and Correct No-Go versus Incorrect No-Go—e.g. times at which the neural components were most discriminant.

Using these markers in time, the EEG sensor data was trial-averaged in a 50 ms window across all epochs that were Correct Go trials, Correct No-Go trials, or Incorrect No-Go creating three grand average ERPs for each subject. The Correct No-Go timings were taken from the Correct Go versus Correct No-Go discrimination. Using these grand average ERP values, sLoreta was used to solve for the most likely current source distribution in the cortex based on the EEG sensor data and array topology. These distributions were used in separate analyses to compare the activation differences between experts and novices using a two-group independent T-test with variance smoothing=0.1.

For estimating the CNV, data were baseline corrected (−200 ms to 0 ms) from S1 and then re-epoched around S2. CNV was measured by taking the average amplitude at the Cz electrode during the final 200 ms of the S1-S2 interval. To estimate the pre-pitch occipital alpha power, a similar analysis method was followed as Lou et al (Lou, et al., 2014). For each subject, the ICA component with a posterior scalp distribution and the highest ratio of alpha-power (8-12 Hz) to that of surrounding frequencies (6-14 Hz) was selected. This ICA component was band pass filtered from 8-12 Hz after which the Hilbert transform was applied to obtain the temporal magnitude and phase. Finally for each trial, the average alpha magnitude during the final 200 ms of S1-S2 interval was taken.

Similar to analyzing the behavioral results, mean pre-pitch CNV amplitude and alpha power were analyzed using repeated-measures ANOVAs on each measure using Trial type (four levels: Correct Go, Correct No-Go, Incorrect No-Go, Incorrect Go) as the within-subject factor and group (expert/novice) as the between-subject factor. The Greenhouse-Geisser (GG) epsilon correction was applied to adjust the degrees of freedom of the F ratios where necessary.

Tables 2 and 3 show the average number of trials for each trial type. A two-way ANOVA on the response times showed a significant effect for the Group ($F(1,17)=26.98, p<0.001$, $\eta 2=0.607$) and the Group×Trial interaction ($F(1,17)=5.64$, $p=0.03$, $\eta 2=0.0087$). Trial type ($F(1,17)=2.6, p=0.13$, $\eta 2=0.004$) did not pass the significance threshold of $p<0.05$.

The two-way ANOVA for error rates showed a significant main effect for Group ($F(1,17)=9.55, p=0.007$, $\eta 2=0.226$), Trial Type ($F(1,17)=132.7, p<0.001$, $\eta 2=0.79$), and the Group×Trial interaction ($F(1,17)=5.89, p=0.027$, $\eta 2=0.14$).

Figure 11:
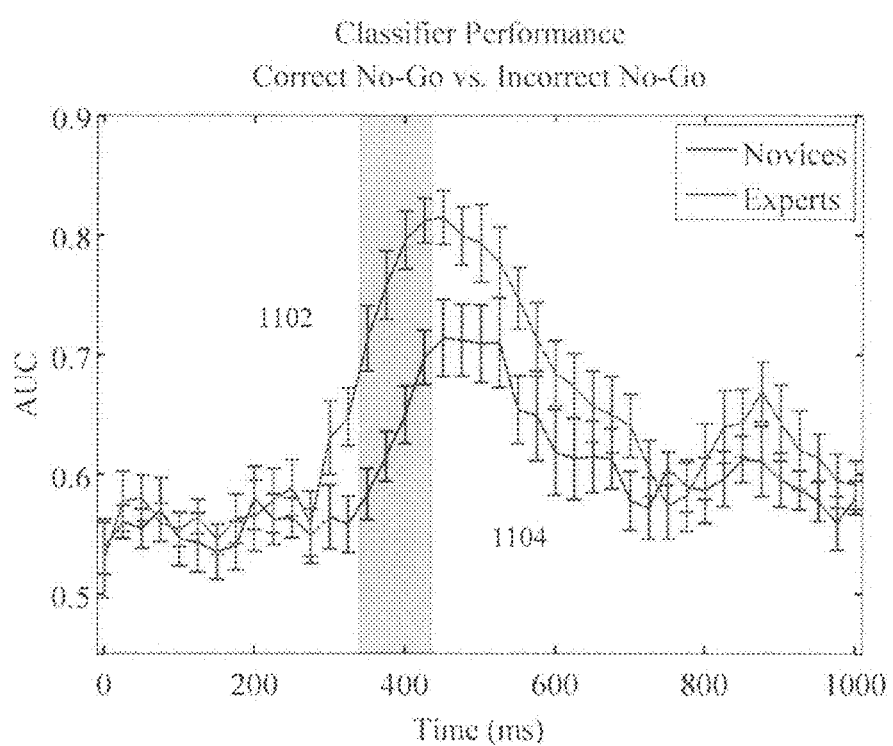
FIG. 11 illustrates the mean classifier performance for discriminating Correct No-Go trials versus Incorrect No-Go trials in accordance with an exemplary embodiment of the disclosed subject matter. The shaded region represents significant (P<0.05 FDR Corrected) windows of performance difference between experts and novices. Experts are plotted at 1102 and novices are plotted at 1104.
Figure 12:
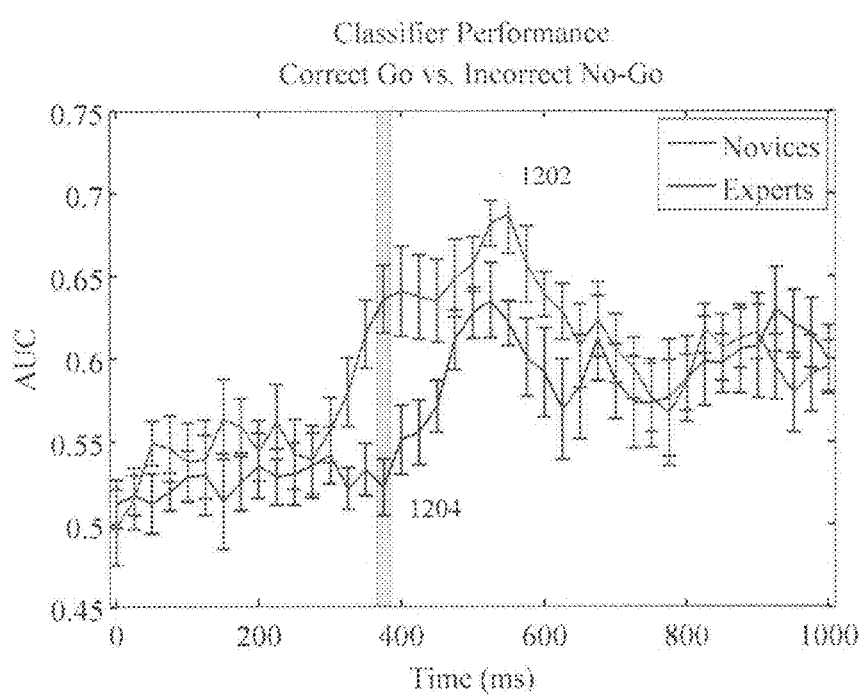
FIG. 12 illustrates the mean classifier performance of for discriminating Correct Go trials versus Incorrect No-Go trials in accordance with an exemplary embodiment of the disclosed subject matter. The shaded region represents significant (P<0.05 FDR Corrected) windows of performance difference between experts and novices. Experts are plotted at 1202 and novices are plotted at 1204.

For another analysis, only considered behaviorally correct trials were considered. However, the same analysis was run for the comparisons of Correct Go versus Incorrect No-Go and Correct No-Go versus Incorrect No-Go trials, as shown in FIGS. 11 and 12. Classification analysis using Incorrect Go trials were not run because of the small number of trials for experts (see Tables 3 and 4) as well as the mixing of incorrect omissions and late commissions that make up the Incorrect Go trials.

groups t-test at each window was computed. Shaded regions indicated significant differences ($p<0.05$ FDR corrected) in discrimination activity between experts and novices. Experts show significantly higher discrimination than novices from 325 to 425 ms.

Figure 14:
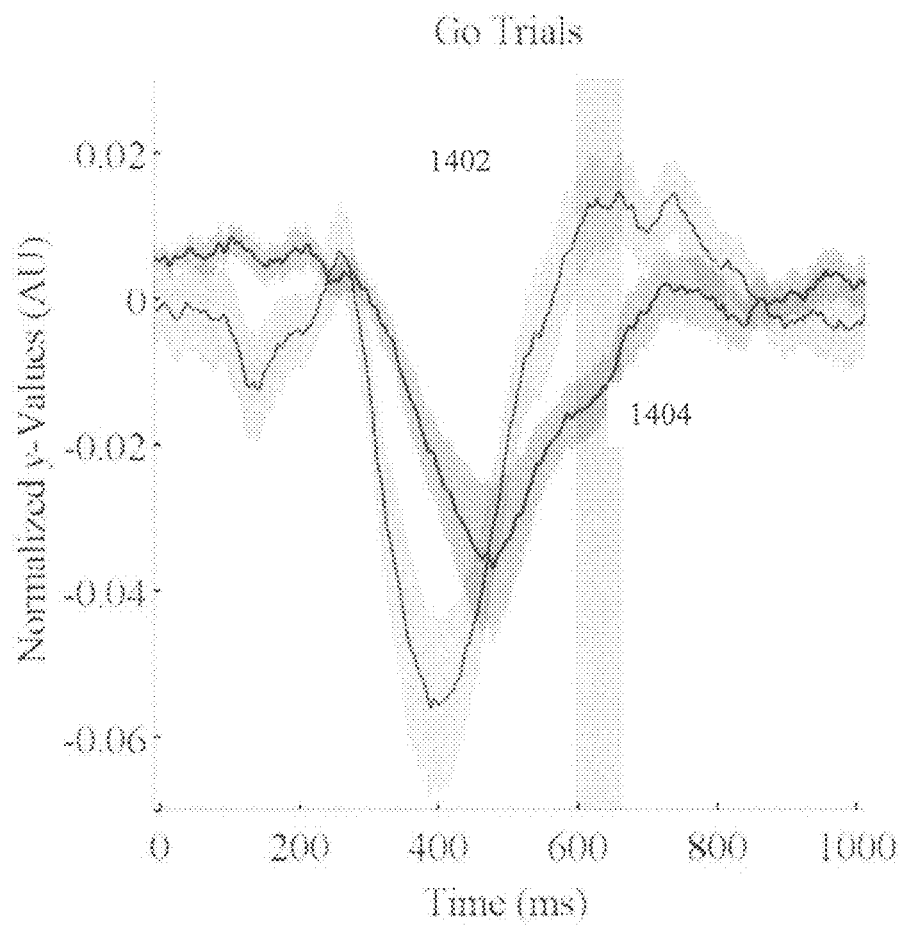
FIG. 14 illustrates the time series of experts versus novices for Go trials in accordance with an exemplary embodiment of the disclosed subject matter. Experts are plotted at 1402 and novices are plotted at 1404.
Figure 15:
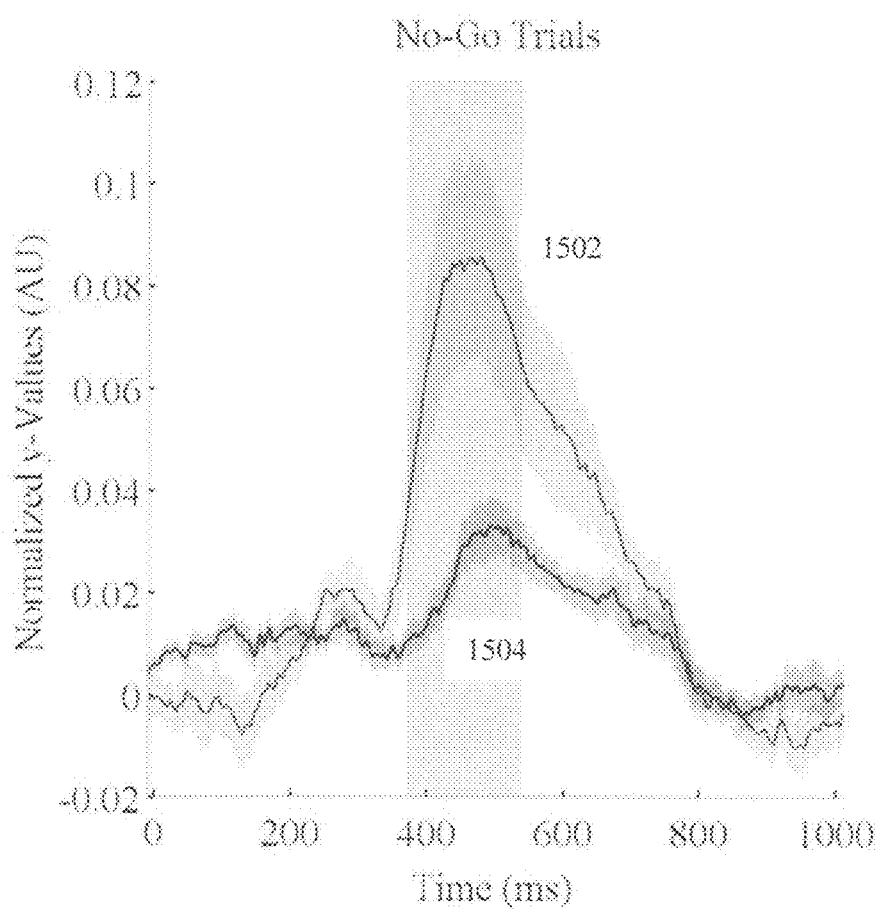
FIG. 15 illustrates the time series of experts versus novices for No-Go trials in accordance with an exemplary embodiment of the disclosed subject matter. Experts are plotted at 1502 and novices are plotted at 1504.

While there are significant differences between experts and novices in the discrimination space, further investigation was undertaken to determine if this stronger discrimination is from expert/novice differences in the Go or No-Go trials. To this end, each subject's max discriminating classifier was used to create normalized y-values averaged across trials from 0 to 1000 ms from onset of stimulus. Each subject's time series was then averaged within group for both Go (FIG. 14) and No-Go (FIG. 15) trials. For Go trials, novices had significantly lower (stronger Go response) y's from 598 to 660 ms ($p<0.05$ FWE corrected), while for No-Go trials; experts had significantly higher y's from 371 to 535 ms ($p<0.05$ FWE corrected).

Figure 16:
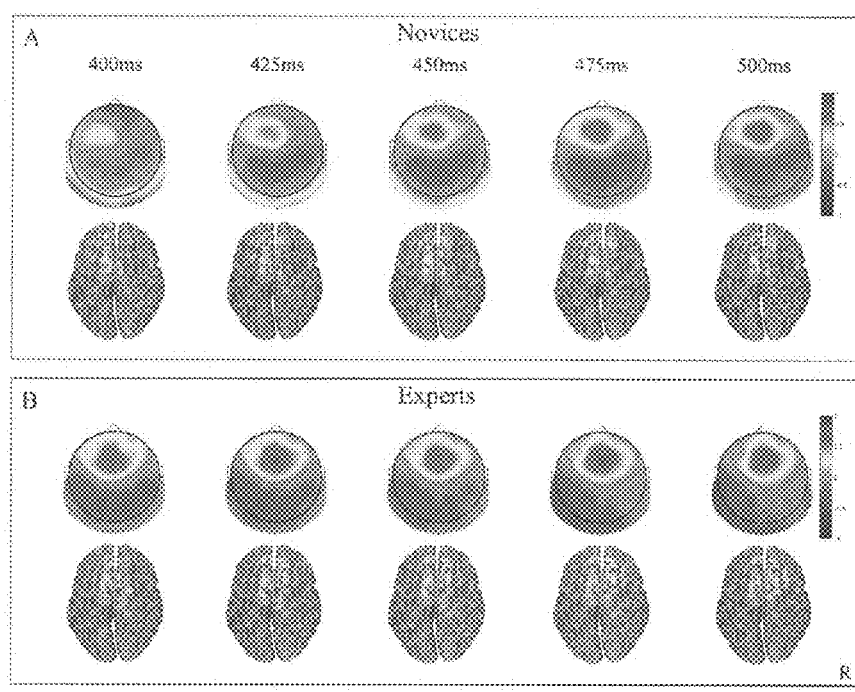
FIG. 16 shows group mean stimulus-locked forward models as scalp and cortical plots illustrates the time series of experts versus novices for Go trials in accordance with an exemplary embodiment of the disclosed subject matter.

Group mean stimulus-locked forward models, shown as scalp and cortical source plots, are given in FIG. 16. Plots are of selected time points (400-500 ms) for both novices and experts, where the center of the discrimination window is indicated at the top of each column. Dark red and blue colors indicate strong correlation of the discriminatory component with the measured scalp activity. The two main sources of discrimination are consistently located in the central frontal and parietal regions of the scalp plots.

The temporal windows having the maximum AUC for each subject were identified. It was found that experts had a mean maximum AUC at 447+/−45 ms while the novices had

TABLE 2

|  | Expert 1 | Expert 2 | Expert 3 | Expert 4 | Expert 5 | Expert 6 | Expert 7 | Expert 8 | Expert 9 |
| --- | --- | --- | --- | --- | --- | --- | --- | --- | --- |
| Correct Go | 239 | 200 | 243 | 191 | 200 | 209 | 214 | 223 | 233 |
| Correct NoGo | 77 | 83 | 106 | 73 | 70 | 74 | 101 | 104 | 114 |
| Incorrect NoGo | 75 | 60 | 63 | 55 | 83 | 84 | 53 | 59 | 49 |
| Incorrect Go | 15 | 13 | 14 | 8 | 30 | 17 | 26 | 20 | 21 |
| Total | 406 | 356 | 426 | 327 | 383 | 384 | 394 | 406 | 417 |

TABLE 3

|  | Novice 1 | Novice 2 | Novice 3 | Novice 4 | Novice 5 | Novice 6 | Novice 7 | Novice 8 | Novice 9 | Novice 10 |
| --- | --- | --- | --- | --- | --- | --- | --- | --- | --- | --- |
| Correct Go | 229 | 187 | 206 | 183 | 211 | 206 | 163 | 165 | 216 | 185 |
| Correct NoGo | 64 | 84 | 106 | 114 | 119 | 91 | 71 | 87 | 76 | 82 |
| Incorrect NoGo | 100 | 71 | 50 | 36 | 57 | 84 | 85 | 78 | 90 | 82 |
| Incorrect Go | 31 | 41 | 44 | 54 | 47 | 59 | 75 | 77 | 39 | 72 |
| Total | 424 | 383 | 406 | 387 | 434 | 440 | 394 | 407 | 421 | 421 |

Figure 13:
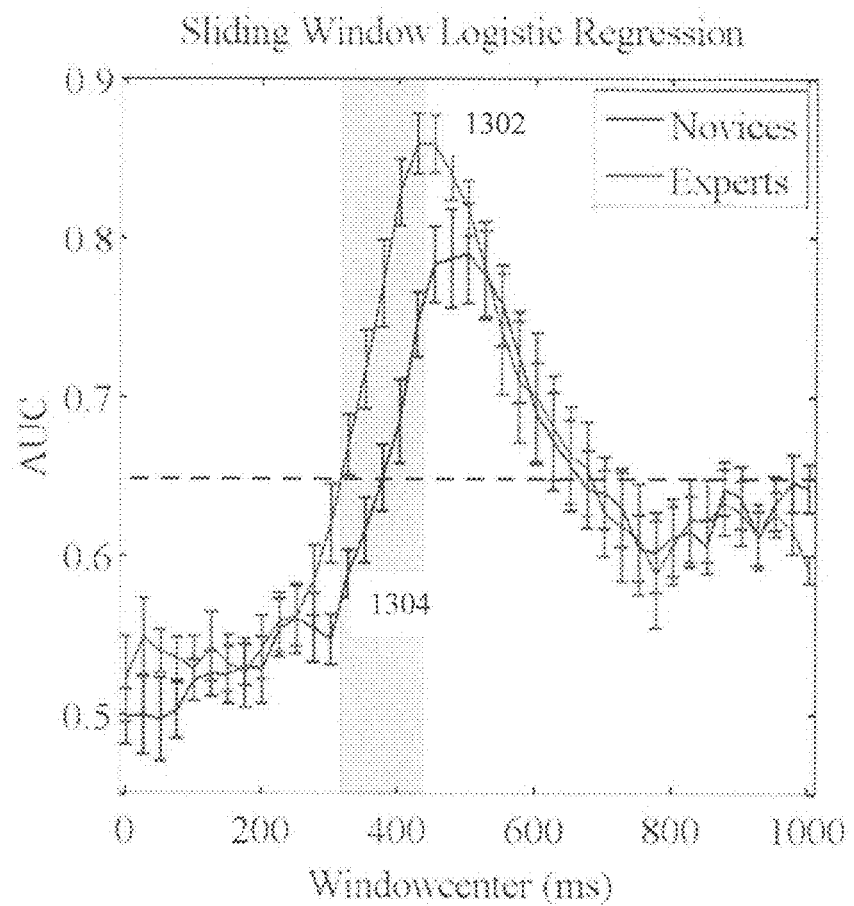
FIG. 13 illustrates the mean performance for stimulus-locked EEG components discriminative of Correct Go versus Correct no-Go discrimination trials in accordance with an exemplary embodiment of the disclosed subject matter. Experts are plotted at 1302 and novices are plotted at 1304.
Figure 17A:

FIG. 13 shows the mean (across subjects, separated by group) performance (area under the ROC curve: AUC) for stimulus-locked EEG components discriminative of Correct Go vs. Correct No-Go discrimination trials. Experts and novices had similarly shaped discrimination curves, however experts exhibited an earlier rise and larger peak than novices. Both groups showed no significant early discrimination (discrimination before 300 ms), however discrimination rose sharply to a maximum AUC of 0.86 at 450 ms for experts and 0.79 at 500 ms for novices. The expert's discrimination curve also was shifted 75 ms earlier relative to that for the novices. To test for significant discrimination differences between experts and novices, an independent a mean maximum AUC at 495+/−55 ms ($t=2.043, p=0.057$, Cohen's $d=0.9385$, Independent Groups T-test) for the Correct Go versus Correct No-Go discrimination. For the Correct No-Go versus Incorrect No-Go discrimination, experts had a mean maximum AUC at 475+/−54 ms while the novices had a mean maximum AUC at 494+/−46 ms ($t=0.7612, p=0.45$, Cohen's $d=0.3497$, Independent Groups T-test) (FIG. 11). Using the EEG data from these subject-specific time windows, the source distributions were determined using sLoreta as explained above. For the first source localization, a paired t-test for Correct Go vs. Correct No-Go was performed across both experts and novices. The resulting t-distribution is shown in FIG. 17A. A permutation test (10000 permutations) was performed to establish significance levels (p<0.05) for the null hypothesis of no difference in activity between Go and No-Go trials. Significant cortical source distributions in Brodmann areas 6 and 8 were found, which include the frontal eye fields and the pre-supplemental motor area (peak MNI coordinates—X=−5 mm, Y=40 mm, Z=50 mm).

Figure 17B:
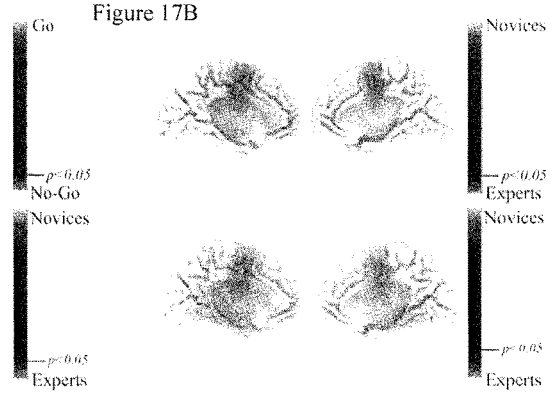
Figure 17C:
Figure 17E:

For the second source localization, a group t-test between experts and novices of the within subject paired difference between Correct Go and Correct No-Go source distributions was performed. As for the first source localization, permutation testing was performed to establish significance. FIG. 17B shows regions where experts have stronger cortical neural generators than novices (peak MNI coordinates—X=−5 mm, Y=−5 mm, Z=50 mm). Significant regions include the Anterior Cingulate Cortex (ACC) and Supplementary Motor Area (SMA). Group t-tests were conducted for differences between experts and novices in Correct Go, Correct No-Go, and Incorrect No-Go trials separately. For Correct Go trials (FIG. 17C), experts had significantly stronger cortical source distributions (peak MNI coordinates—X=15 mm, Y=55 mm, Z=−15 mm) in frontal orbital gyrus (BA 11) and fusiform gyrus (BA 37), while in Correct No-Go trials (FIG. 17D) a similar cluster to FIG. 4B is shown, with activation in the SMA and ACC (peak MNI coordinates—X=−5 mm, Y=−10 mm, Z=50 mm). Finally, experts had significantly stronger cortical source distributions for Incorrect No-Go trials (peak MNI coordinates—X=−55 mm, Y=0 mm, Z=−30 mm) in the middle temporal gyrus (BA 21), superior temporal gyrus (BA 38), and superior frontal gyms (BA 10/11).

A two-way ANOVA was performed for pre-stimulus Alpha power, however results were insignificant for all factors analyzed. Experts had a lower but insignificant difference from novices ($F(1,17)=0.750, p>0.05$, $\eta 2=0.0415$). Trial type ($F(3,51)=0.28$, $p>0.05$, $\eta 2=0.00028$) and the interaction of Group×Trial Type ($F(3,51)=2.72$, $p>0.05$, $\eta 2=0.0028$) was insignificant.

Figure 18:
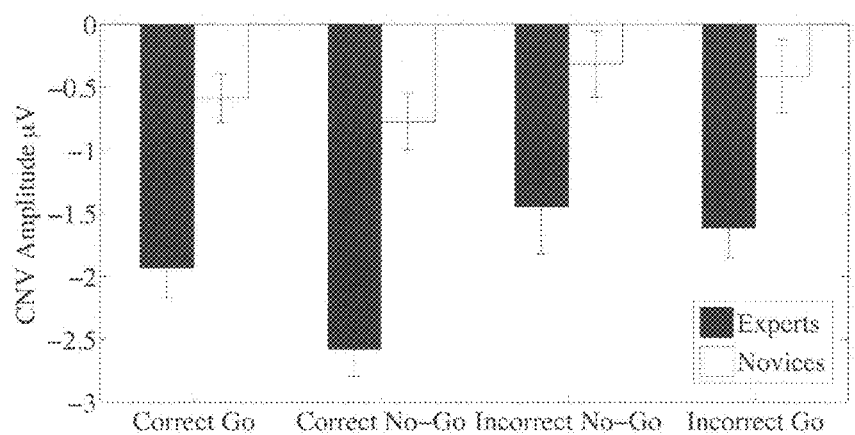
FIG. 18 illustrates the average contingent negative variation amplitude for experts and novices across four trial types in accordance with an exemplary embodiment of the disclosed subject matter.
Figure 19:
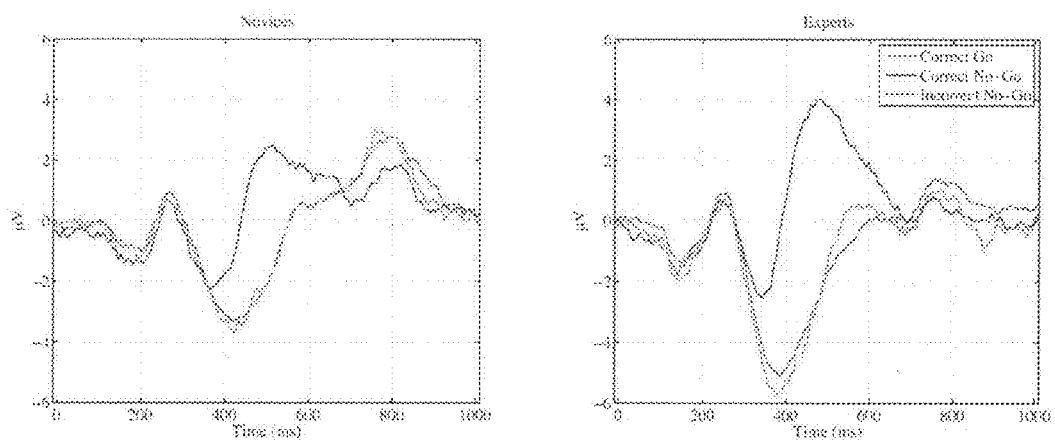
FIG. 19 shows novice and expert event related potentials (EPRs) at electrode Fz in accordance with an exemplary embodiment of the disclosed subject matter. Correct Go, Correct No-Go, and Incorrect No-Go trials are all plotted for both novices and experts.
Figure 20:
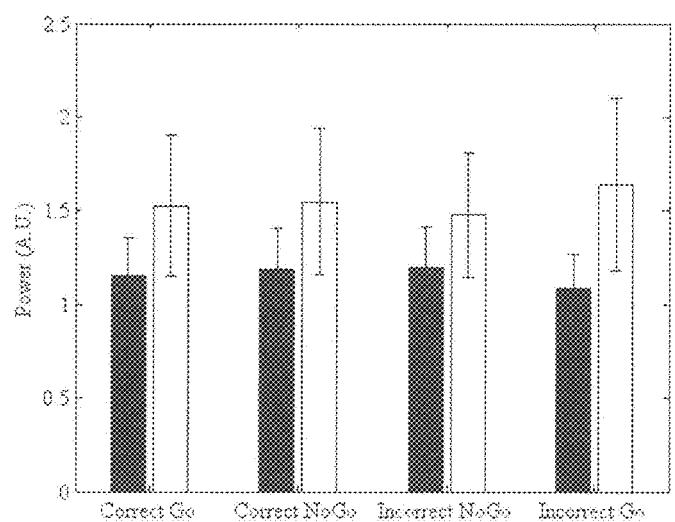
FIG. 20 shows pre-stimulus alpha power results for both experts (black bars) and novices (white bars). No significant differences across groups or trial types are seen.

FIG. 18 shows the average CNV amplitude for experts and novices across the four trial types. A two way ANOVA for CNV amplitude showed a significant main effect for the Group ($F(1,17)=30.66, p<0.001$, $\eta 2=0.4512$) and Trial type ($F(3,51)=4.756, p=0.0053, \eta 2=0.132$, GGe=0.648), while the Group×Trial interaction ($F(3,51)=0.948, p>0.05, \eta 2=0.029$) did not pass the significance threshold. An analysis of the main effect of trial type showed Correct No-Go trials were significantly different from Incorrect No-Go trials ($z=3.526$, $p=0.003$) and significantly different from Incorrect Go trials ($z=3.005, p=0.019$). An additional contrast for correct versus incorrect trials that was also significant was included ($z=3.195, p=0.0098$).

The foregoing merely illustrates the principles of the disclosed subject matter. Various modifications and alterations to the described embodiments will be apparent to those skilled in the art in view of the inventors' teachings herein. Features of existing EEG systems and methods can be seamlessly integrated into the exemplary embodiments of the disclosed subject matter or a similar system. It will thus be appreciated that those skilled in the art will be able to devise numerous systems and methods which, although not explicitly shown or described herein, embody the principles of the disclosed subject matter and are thus within its spirit and scope.

We claim:

1. A system for evaluating a subject's response when presented with a task related to a stimulus having a trajectory, the system comprising:
   a brain activity sensor configured to measure neural response data generated by the subject when presented with the task related to the stimulus having the trajectory;
   a signal processing system comprising at least one processor configured to identify one or more neural discriminators associated with the task based on the neural response data using a classifier, wherein the classifier is configured to calculate the one or more neural discriminators that discriminates between two or more task conditions; and
   an output device comprising at least one of a monitor or a printer configured to provide information based on the neural discriminators for purposes of evaluation.

2. The system of claim 1, wherein the brain activity sensor comprises an array of brain activity sensors.

3. The system of claim 1, wherein the brain activity sensor comprises an electroencephalography sensor.

4. The system of claim 1, wherein the brain activity sensor comprises a functional magnetic resonance imaging sensor.

5. The system of claim 1, wherein the brain activity sensor comprises a near infrared sensor.

6. The system of claim 1, wherein the two or more task conditions comprise a correct decision and/or an incorrect decision.

7. The system of claim 1, wherein a spatial distribution of the neural response data is applied to the classifier to learn an optimal linear discriminator.

8. A system for evaluating a subject's response when presented with a task related to a stimulus having a trajectory, the system comprising:
   a brain activity sensor configured to measure neural response data generated by the subject when presented with the task related to the stimulus having the trajectory;
   at least one processor;
   a computer-readable medium storing instructions that, when implemented, cause the at least one processor to identify one or more neural discriminators associated with the task based on the neural response data using a classifier, wherein the classifier is configured to calculate the one or more neural discriminators that discriminates between two or more task conditions; and
   an output device comprising at least one of a monitor or a printer configured to provide information based on the neural discriminators for purposes of evaluation.

9. The system of claim 8, wherein the two or more task conditions comprise a correct decision and/or an incorrect decision.

10. The system of claim 8, wherein a spatial distribution of the neural response data is applied to the classifier to learn an optimal linear discriminator.

* * * * *